(12) United States Patent
Hayes

(10) Patent No.: US 10,856,915 B2
(45) Date of Patent: Dec. 8, 2020

(54) SPONDYLISTHESIS REDUCTION SYSTEM

(71) Applicant: Alphatec Spine, Inc., Carlsbad, CA (US)

(72) Inventor: Stanley Kyle Hayes, Mission Viejo, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 254 days.

(21) Appl. No.: 15/875,612

(22) Filed: Jan. 19, 2018

(65) Prior Publication Data

US 2018/0153586 A1 Jun. 7, 2018

Related U.S. Application Data

(62) Division of application No. 14/539,567, filed on Nov. 12, 2014, now Pat. No. 9,907,583.

(60) Provisional application No. 61/902,993, filed on Nov. 12, 2013.

(51) Int. Cl.
  *A61B 17/70* (2006.01)
  *A61B 17/68* (2006.01)

(52) U.S. Cl.
  CPC ........ *A61B 17/708* (2013.01); *A61B 17/7032* (2013.01); *A61B 2017/681* (2013.01)

(58) Field of Classification Search
  CPC .......................... A61B 17/708; A61B 17/7077
  See application file for complete search history.

(56) References Cited

U.S. PATENT DOCUMENTS

| | | | |
|---|---|---|---|
| 5,358,504 A * | 10/1994 | Paley | A61B 17/66 606/105 |
| 6,648,891 B2 * | 11/2003 | Kim | A61B 17/0206 606/102 |
| 2008/0119862 A1 | 5/2008 | Wicker et al. | |
| 2011/0077690 A1 | 3/2011 | Shin et al. | |
| 2013/0172947 A1 | 7/2013 | Greenberg | |
| 2013/0211453 A1 | 8/2013 | Lenke et al. | |
| 2015/0066088 A1 | 3/2015 | Brinkman et al. | |

* cited by examiner

*Primary Examiner* — Olivia C Chang
(74) *Attorney, Agent, or Firm* — Robert Winn

(57) ABSTRACT

A system for reducing deformities of the vertebrae in the spine includes a first reduction assembly, a second reduction assembly, and a reduction drive assembly. The first reduction assembly is configured for attachment to a first reduction tower that attaches to a first vertebra. The second reduction assembly is configured for attachment to a second reduction tower that attaches to a second vertebra. The reduction drive assembly includes an arcuate rack gear operably coupling the first reduction assembly to the second reduction assembly to translate the first reduction assembly relative to the second reduction assembly along an arcuate path in a first plane.

20 Claims, 33 Drawing Sheets

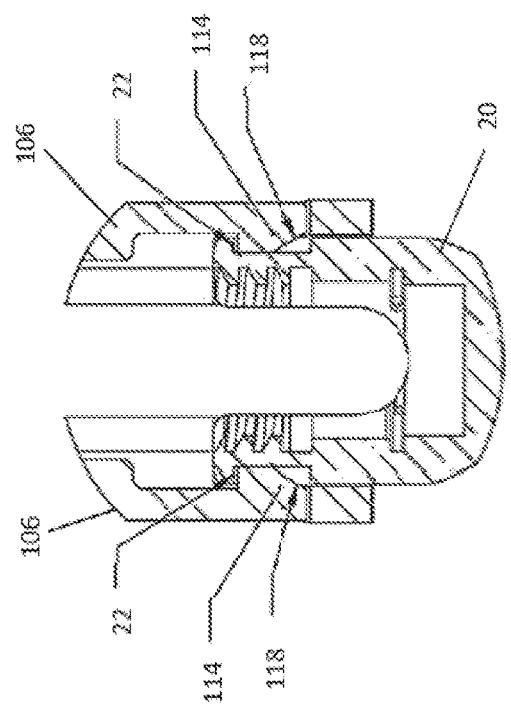
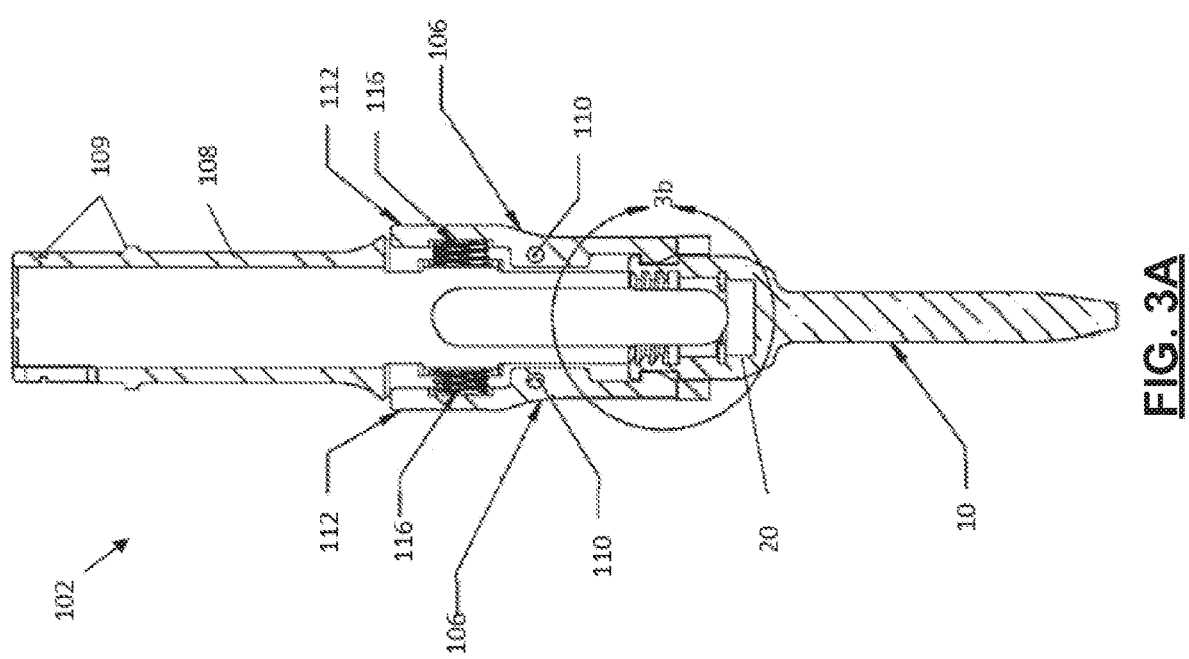
FIG. 3B
FIG. 3A

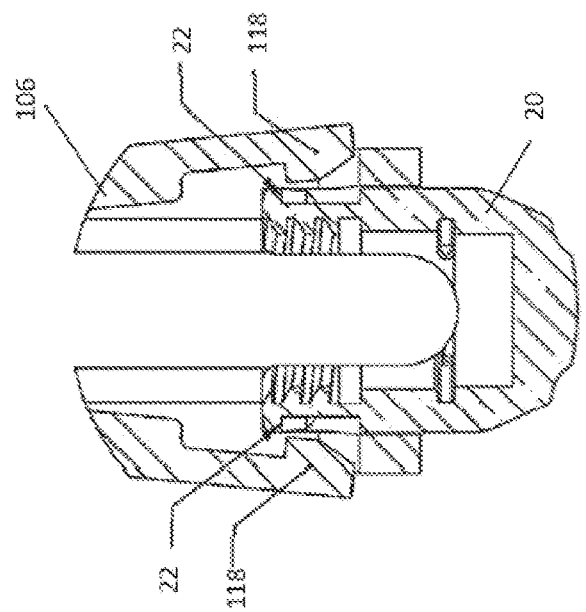
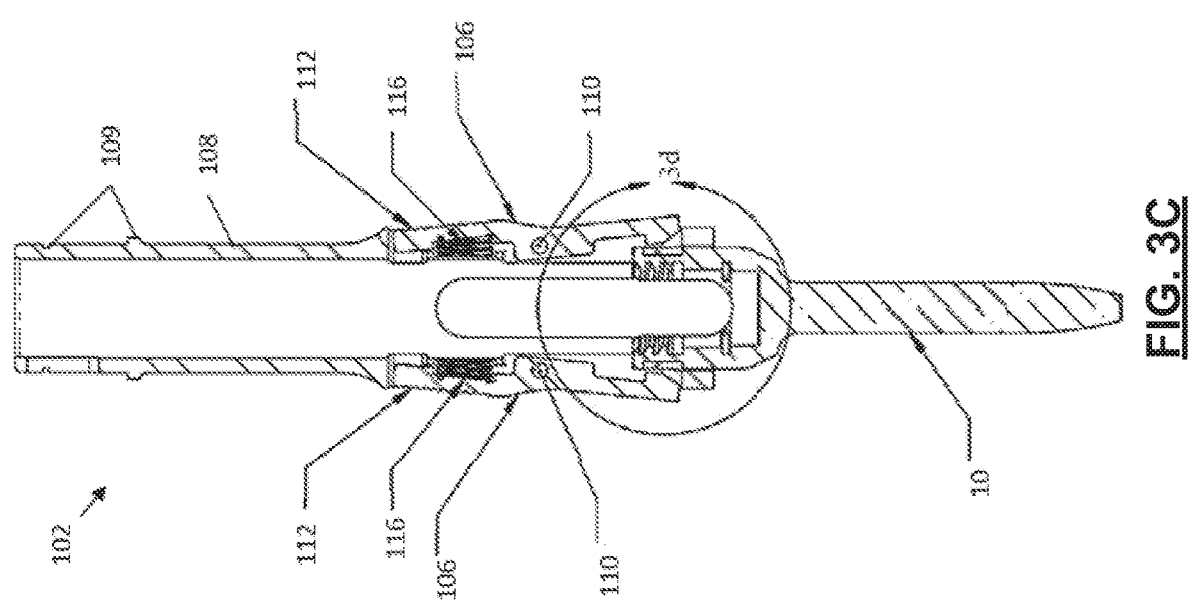
FIG. 3D
FIG. 3C

SPONDYLISTHESIS REDUCTION SYSTEM

CROSS-REFERENCE TO RELATED APPLICATIONS

The present application is a divisional application of U.S. patent application Ser. No. 14/539,567 filed on Nov. 12, 2014, which in turn claims priority to U.S. Provisional Patent Application Ser. No. 61/902,993 filed Nov. 12, 2013, which is incorporate herein by reference in its entirety.

TECHNICAL FIELD

The present disclosure generally relates to the field of spinal orthopedics, and more particularly to instruments for reducing spondylolisthesis.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

Spondylolisthesis is the anterior or posterior displacement of a vertebra of the vertebral column in relation to the vertebra below. In the lower region of the back where the lumbar vertebrae meet the sacrum, spondylolisthesis may occur more frequently. For example, at the L5-S1 level, the fifth lumbar vertebra may slip forward or in the anterior direction relative to the first level of the sacrum. Treatment for spondylolisthesis depends on the severity of the slippage. For severe cases, surgical correction is required.

Various systems and methods are known to alleviate and correct spondylolisthesis. For example, German Patent 41 27 303, filed Aug. 17, 1991 (also disclosed in European Patent No. 0528177, filed Jul. 16, 1992) to Aesculap A G, discloses such a device. Other devices include U.S. Pat. No. 6,565,568, filed Sep. 28, 2000 to Rogozinski and U.S. Pat. Pub. No. 2009/0216237, filed Jun. 30, 2006 to Frezal et al. However, some of these systems may be difficult to maneuver, attach, and remove from screw heads. Some of these systems may make it difficult to insert and secure fixation rods after correcting the slippage without removing portions of the systems.

The present invention seeks to overcome these problems, and others.

SUMMARY

Provided herein are systems, apparatuses, and methods for reducing deformities in the spine.

A system for reducing deformities of the vertebrae in the spine includes a first reduction assembly, a second reduction assembly, and a reduction drive assembly. The first reduction assembly is configured for attachment to a first reduction tower that attaches to a first vertebra. The second reduction assembly is configured for attachment to a second reduction tower that attaches to a second vertebra. The reduction drive assembly includes an arcuate rack gear operably coupling the first reduction assembly to the second reduction assembly to translate the first reduction assembly relative to the second reduction assembly along an arcuate path in a first plane.

In other features, the first reduction assembly is operably coupled with the arcuate rack gear to enable translation of the first reduction assembly relative to the arcuate rack gear along a linear path in a second plane that is parallel to the first plane. In yet other features, the first reduction assembly is operably coupled with the arcuate rack gear to enable rotation relative of the first reduction assembly relative to the arcuate rack gear in a third plane that is perpendicular to the first plane. In still other features, the first reduction assembly is configured to rotatably couple with a proximal end of the first reduction tower to permit rotation relative to the first reduction tower in a fourth plane perpendicular to the second plane.

In other features, the second reduction assembly is configured to rotatably couple with a proximal end of the second reduction tower to permit rotation relative to the second reduction tower in a fifth plane perpendicular to the first plane. In yet other features, the arcuate rack gear is pivotally coupled with a receiver that receives a load transfer link of the first reduction assembly.

In still other features, the reduction drive assembly comprises a reduction lever coupled with a pinion gear configured to engage and drive the arcuate rack gear. The reduction drive assembly includes a reduction pawl to restrict movement of the arcuate rack gear to a single direction. The reduction drive assembly includes a locking pawl to lock the arcuate rack gear in place.

In yet other features, the reduction drive assembly is configured to translate the arcuate rack gear along a curved path having a center of rotation behind and below a distal end of the second tower assembly.

A system for reducing deformities in the spine includes a first tower assembly, a first reduction assembly, a second tower assembly, and a second reduction assembly. The first reduction assembly is operably coupled to a proximal end of the first tower assembly. The second reduction assembly is operably coupled to a proximal end of the second tower assembly. The second reduction assembly further includes a reduction drive assembly. The reduction drive assembly includes a rack having an arcuate profile driven by a pinion gear. The reduction drive assembly is operably coupled to the first reduction assembly such that the reduction drive assembly transmits a leverage and causes relative movement of the first tower assembly from the second tower assembly from an unreduced state into a reduce state.

In other features, the first reduction assembly further includes a load transfer link receiver and the second reduction assembly further comprises a load transfer link member. The load transfer link member and the load transfer link receiver are operably engaged and freely translatable relative to one another. The load transfer link member is disposed at an end of the arcuate rack.

In other features, a locking lever operably couples to the pinion gear. In yet other features, the first reduction assembly and the second reduction assembly are operably coupled by a load transfer link member, at least a portion of the member having stepped features to define a ratcheted portion, and a load transfer link receiver, at least a portion of the receiver being configured to engage the ratcheted portion of the member.

In still other features, the arcuate rack translates in a single plane relative to the second reduction assembly. In yet other features, the arcuate rack translates along a curved path having a center of rotation behind and below a distal end of the second tower assembly.

In yet other features, the reduction drive assembly further includes a reduction lever operably coupled to the pinion and the second reduction assembly further includes a handle member. In still other features, the reduction drive assembly further includes a reduction pawl operably coupled to the reduction lever and the pinion and a locking pawl operably coupled to the rack.

BRIEF DESCRIPTION OF THE DRAWINGS

In the accompanying figures, like elements are identified by like reference numerals among the several preferred embodiments of the present invention.

FIGS. 3A-3D are cross-sectional views of a tower assembly of the system and one of the bone screws according to the principles of the present disclosure.

DETAILED DESCRIPTION OF PREFERRED EMBODIMENTS

Figure 1A:
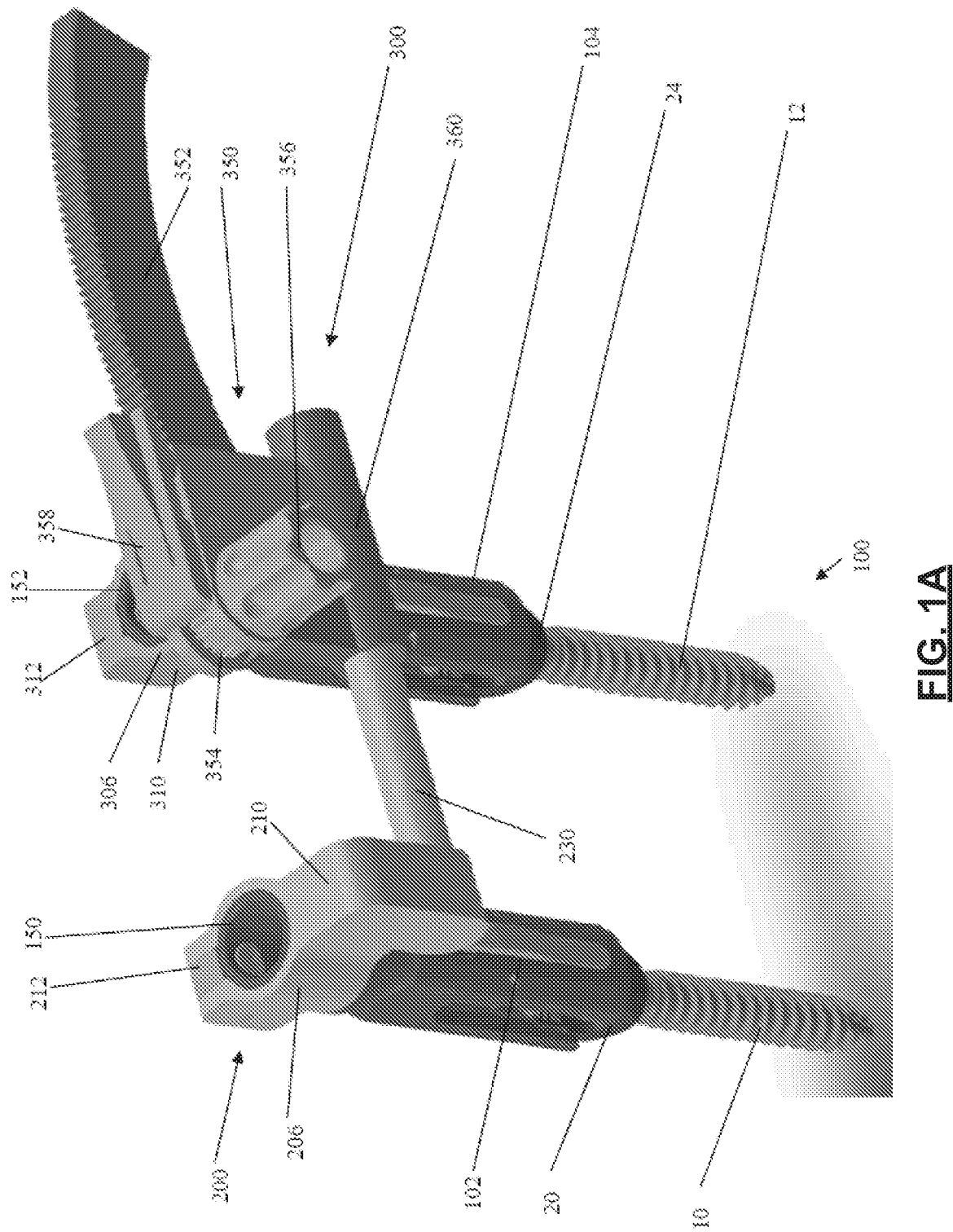
FIG. 1A is a first isometric view of the system of the present invention.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instruments described herein. A proximal end refers to the end of an instrument nearer to an operator of the instrument when the instrument is being used. A distal end refers to the end of a component further from the operator and extending towards the surgical area of a patient and/or the implant.

Reference to the invention may also be described with respect to coronal, sagittal, and transverse axes of the body. The coronal axis refers to an axis running substantially from front (anterior) to back (posterior) of the body and extending through the mid-section. The sagittal axis refers to an axis running substantially from left to right of the body and extending through the mid-section to intersect the coronal axis at a right angle. The transverse axis refers to an axis running substantially from head to toe of the body and crossing the point where the coronal and sagittal axes intersect at a right angle. Furthermore, the coronal, sagittal, and transverse planes refer to the standard definitions associated with each term. Namely, the coronal plane being a plane perpendicular to the coronal axis and formed by the transverse and sagittal axes, the sagittal plane being perpendicular to the sagittal axis and formed by the coronal and transverse axes, and the transverse plane being perpendicular to the transverse axis and formed by the sagittal and coronal axes.

For a mid to high grade spondylolisthesis at the L5-S1 level, the anatomy is exposed and bone screws are placed in the pedicles of the L5 lumbar vertebra bilaterally near the cephalad end of the sacrum. Bone screws are also placed in the sacrum. A system of instruments may be used to reposition the L5 vertebra relative to the S1 level. The system may comprise a set of mirrored tower assemblies which attach to the tops of the screw heads.

Generally speaking, the sacral (second) towers may provide a relative ground reference for the reduction apparatus while the lumbar (first) towers may act as load transfer structures. A drive apparatus mounted to the sacral towers provides forced to produce the necessary anatomical correction. The tower assemblies transmit the leverage generated by the drive apparatus into a posterior load on the L5 vertebral body. The system applies a generally posteriorly directed force to the vertebral body while allowing the vertebral body to travel posteriorly along a path of least resistance. The system may or may not dictate an exact path the vertebral body takes during the reduction procedure. Rods can then be placed in the heads of the bone screws and secured in place without removing the system.

Benefits of the present invention include the ability to attach the tower assemblies and remove them from the screw head in a single action. The present invention may also provide the ability to insert fixation rods and secure them with set screws without removing the towers.

Figure 1B:
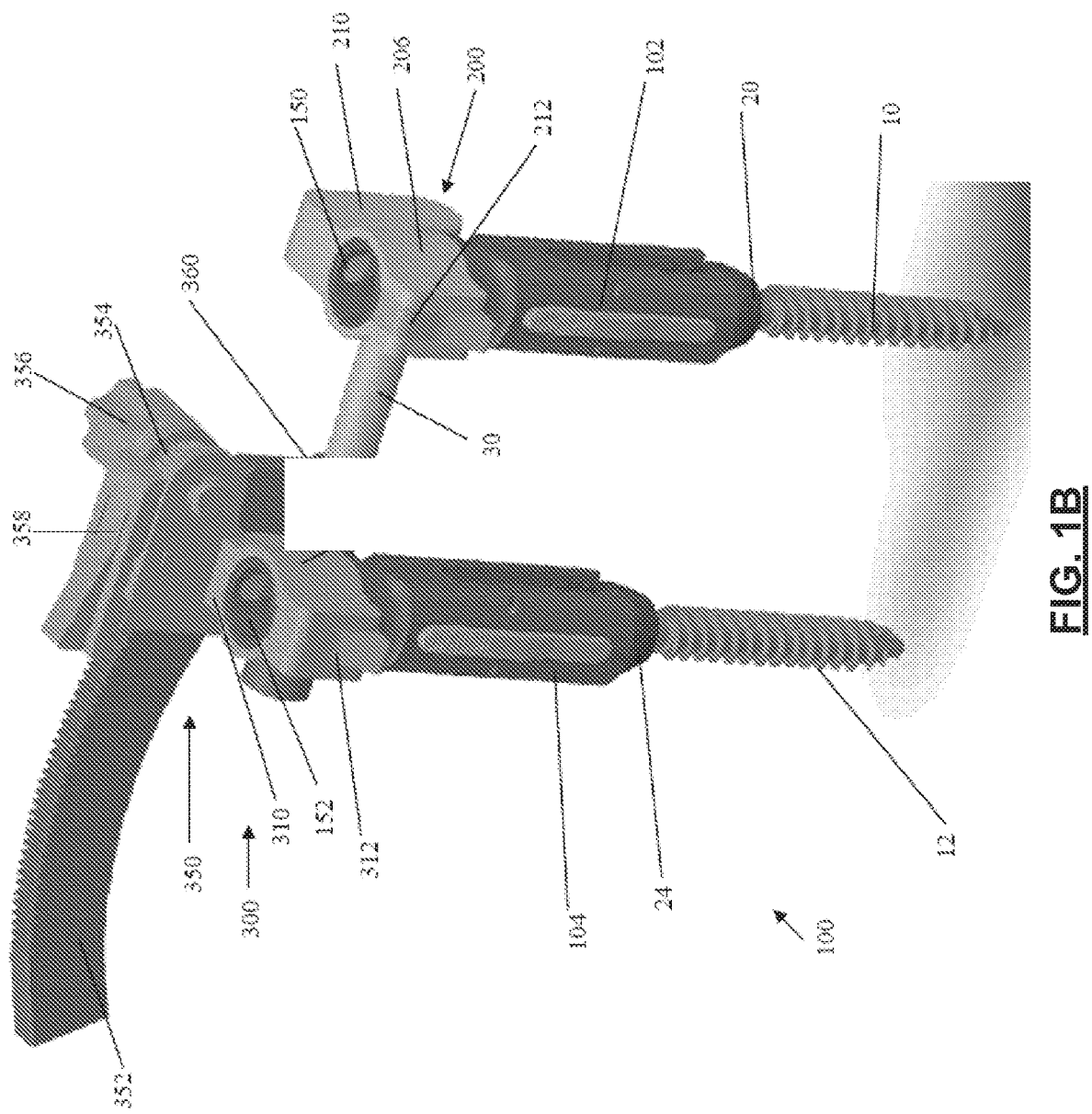
FIG. 1B is a second isometric view of FIG. 1A.

Referring to FIGS. 1-15, a system 100 for correcting spondylolisthesis is disclosed. The system 100 is shown in conjunction with two sets of bone screws inserted into two vertebrae of a spinal column in FIGS. 4A-B and 7-12. As shown in FIGS. 1A and 1B, the system 100 may include first tower assembly 102 and second tower assembly 104. The tower assemblies 102 and 104 may be attached to bone screws at the distal end of the tower assemblies 102 and 104. For example, in FIGS. 2A and 2B, a first set of bone screws 10 has been inserted into a fifth lumbar vertebra L5 and a second set of bone screws 12 has been inserted into the first level of the sacrum 51 through a minimally invasive surgery (MIS) technique, or through any other technique as known in the art. The system 100 may be used in conjunction with a spinal fixation system that includes one or more fixation rods (not shown) disposed through a lumen of the tower assemblies 102 and 104 and setscrews (not shown) to permanently align and rigidly fix two or more levels of the spinal column such as the L5 and 51 levels. Exemplary bone screws and fixation systems may be found in U.S. Pub. No. 2010/0036443 and U.S. Pub. No. 2009/0171391 both of which are incorporated herein by reference in their entirety. Bone screws 10, 12 may comprise polyaxial type screws, monoaxial type screws, or fixed screws, as known in the art.

Although the system 100 of the present disclosure is described herein with reference to the L5 and S1 levels, the system 100 may be used in other regions of the spine where spondylolisthesis or other slippage of vertebral bodies may occur. As shown in FIGS. 1A-B the tower assemblies 102 and 104 may removably couple with sets of bones screws 10 and 12 respectively via MIS procedures, or other procedures as known in the art. The tower assemblies 102 and 104 include a mating feature 109 on the proximal end of the tower assemblies 102 and 104 to couple the towers 102 and 104 to the reduction assemblies 200 and 300 and transmit a leverage generated by the reduction assemblies 200 and 300 to cause relative movement of the tower assembly 102 from tower assembly 104. The first tower assembly 102 may be referred to as a lumbar tower assembly. The second tower assembly 104 may be referred to as a sacral tower assembly. The tower assemblies 102 and 104 may couple to the bone screws 10 and 12 respectively and in substantially similar fashion.

Figure 2A:
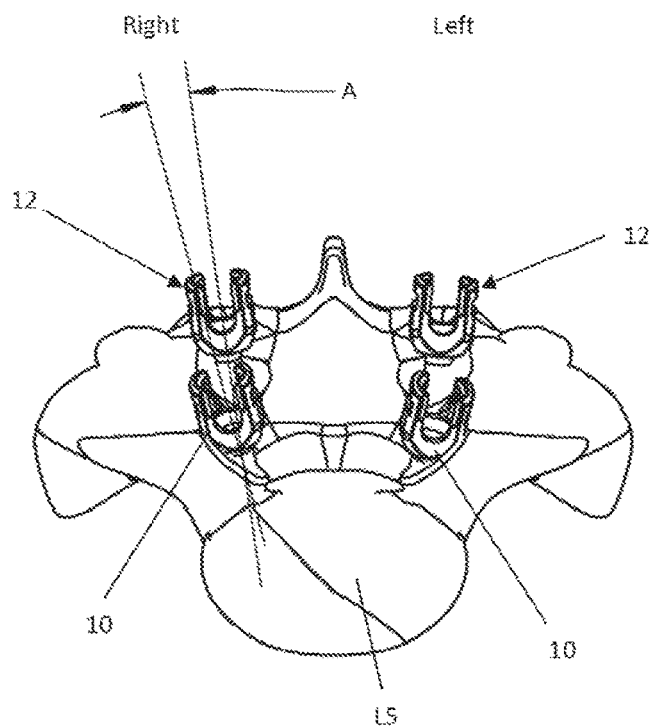
FIG. 2A is a side view of a section of human spine, illustrating displacement of the L5 vertebra due to spondylolisthesis.
Figure 2B:
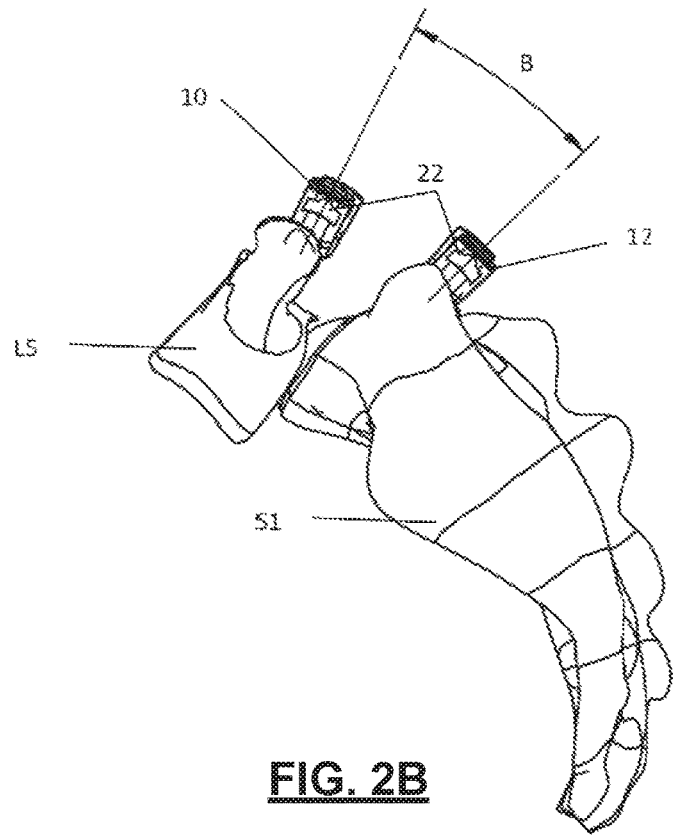
FIG. 2B is a first view of a portion of the spine and associated bone screws for use with the system according to the principles of the present disclosure.

Anatomy and the degree of severity of the spondylolisthesis will vary from patient to patient. Thus, after placement of the bone screws 10, 12, longitudinal axes of the bone screws 10, 12 may not be co-planer when observed from a viewpoint normal to the transverse plane as shown by FIG. 2A. For example, an angle A may be formed by the axes. Additionally, an angle between the longitudinal axes may vary when observed from a viewpoint normal to the sagittal plane as shown by FIG. 2B. For example, an angle B may be formed by the axes. To accommodate for the variations between patients and severity of the spondylolisthesis, various interconnecting elements of the system 100 provide sufficient degrees of freedom to allow for variations in placement and actuation of the system 100. Each tower assembly 102 and 104 may include additional features that enable positioning and alignment of the L5 vertebra relative to the S1 level of the sacrum prior to fixation with the rods. Because each set of tower assemblies includes mirrored components, references throughout this description may refer to left sides and right sides of the system 100 interchangeably. Left and right may indicate the left side and right side from the viewpoint of a patient. Furthermore, each left and right tower assembly 102 and 104 may couple with the bone screws in substantially similar fashion.

As shown in FIGS. 3A-D, a portion of one tower assembly is shown in conjunction with one of the bone screws. For ease of discussion, the description herein will refer to one of the lumbar tower assemblies 102 and one of the L5 vertebra bone screws 10. The lumbar tower assembly 102 may include features to enable single-action coupling with and removal from a receiving portion 20 of the bone screw 10 (receiving portion 24 for bone screw 12). For example, the lumbar tower assembly 102 may include clips 106 in sidewalls 108 of the tower assembly 102. The clips 106 may extend along the length of the sidewall and may pivot on pins 110. Each clip 106 may include a proximal end with grips or pads 112 which may be depressed by the surgeon to actuate the clip 106. Each clip 106 may include a distal end with a projection 114, such as a boss or protrusion that extends radially inward from the clip 106. The projection 114 may engages with a recessed portion 22, such as a bore, pocket, or indentation, of the receiver portion 20 of the bone screw 10. A bias mechanism 116, such as a coil spring, leaf spring, or other elastic mechanism, may position the clip 106 into an engaged or closed position with the receiver portion 20. The surgeon may apply force via the pads 112 to position the clip 106 into a disengaged or open position, wherein the projection 114 disengages the receiver portion 20, thus permitting removal of the tower assembly 102 from the screw 10. The projection 114 may include a ramped surface 118 or taper to facilitate coupling with the receiver portion 20 without actuating the clips 106 to the open position. The proximal end of the tower assemblies 102 and 104 may also include a mating feature 109 as to allow the reduction assembly members 200 and 300 to be operably coupled to the proximal ends of the tower assemblies 102 and 104. The mating feature 109 may protrude into the surface of the sidewalls 108 and may also protrude outwards from the surface of the sidewalls 108, as to provide a lipped and indented mating feature 109 with a space therebetween.

In some embodiments, as shown in FIGS. 1A-B, 3E, 4A-B, and 7-12, the towers 102, 104 may further comprise quick-release engagement features 150, 152. In one embodiment, quick-release engagement features 150, 152 may comprise an aperture through a proximal portion of the wall 108 of the towers 102, 104. The quick-release engagement features 150, 152 may operably engage with a quick-release trigger 212 on the first reduction assembly 200 or a quick-release trigger 312 on the second reduction assembly 300. In some embodiments, the quick-release engagement features 150, 152 and triggers 212, 312 prevent rotation the first and second reduction assemblies 200, 300 relative to the towers 102, 104.

Figure 3E:
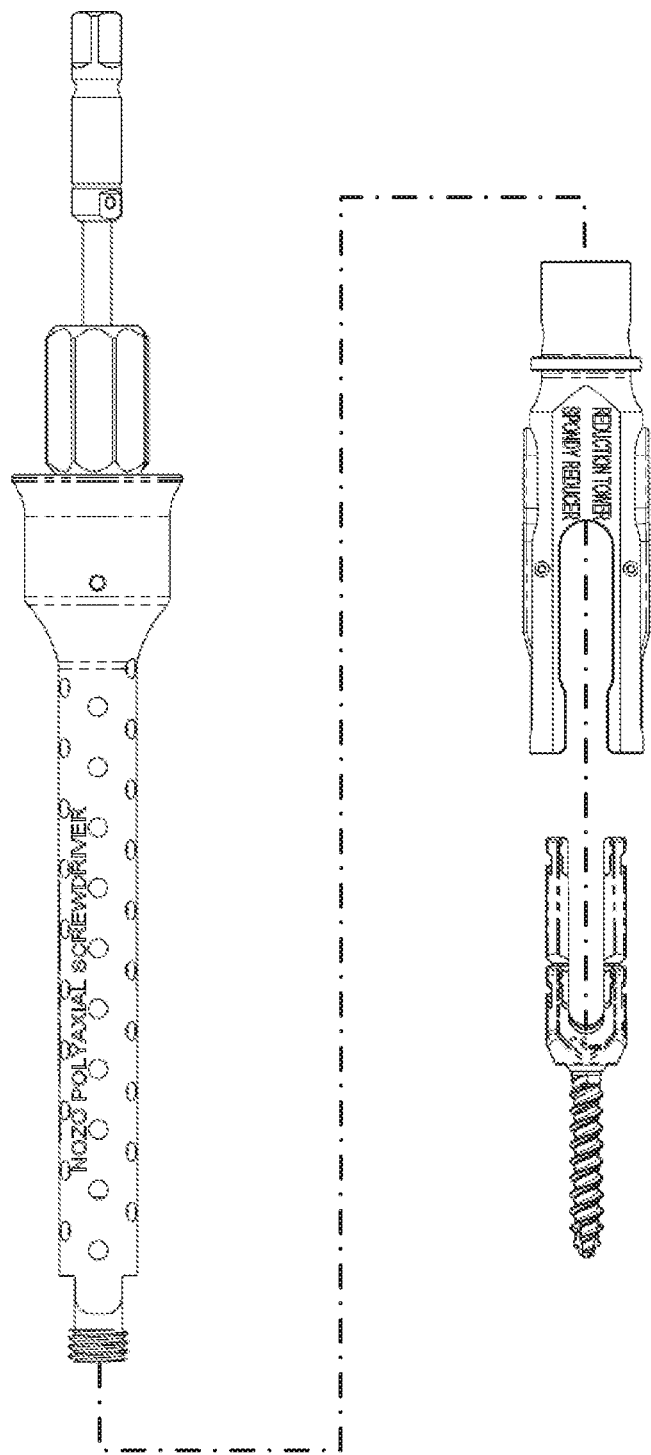
FIG. 3E is an illustration of an exemplary polyaxial screw, tower assembly, and screw driver for use with the present invention.

FIG. 3E illustrates one embodiment of an exemplary pedicle screw 10 and tower 102. The tower 102 may further comprise a quick-release engagement feature 150 (or quick-release engagement feature 152 for tower 104). In one embodiment, quick-release engagement feature 150 may comprise an aperture through a proximal portion of the wall 108 of the tower 102. A driver 80 may be used to install the pedicle screws 10, 12 in the spine. The driver 80 may be any suitable pedicle screw driver, as known in the art. In one embodiment, the driver 80 may configured for MIS type screw insertion.

Figure 4A:
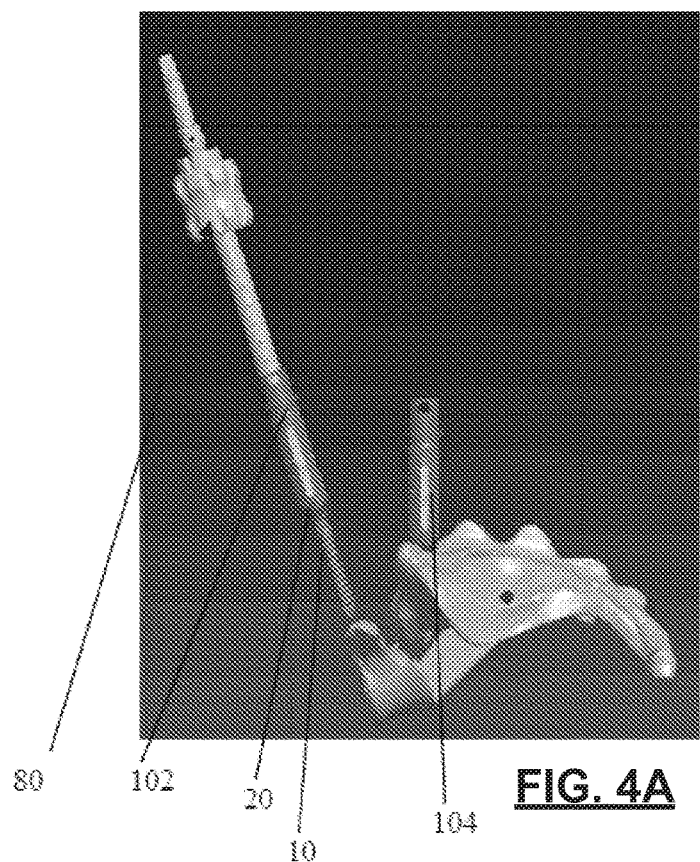
FIGS. 4A-4B illustrate the process of preparing the vertebrae for treatment, by installing the polyaxial screws and towers by use of the driver.
Figure 4B:
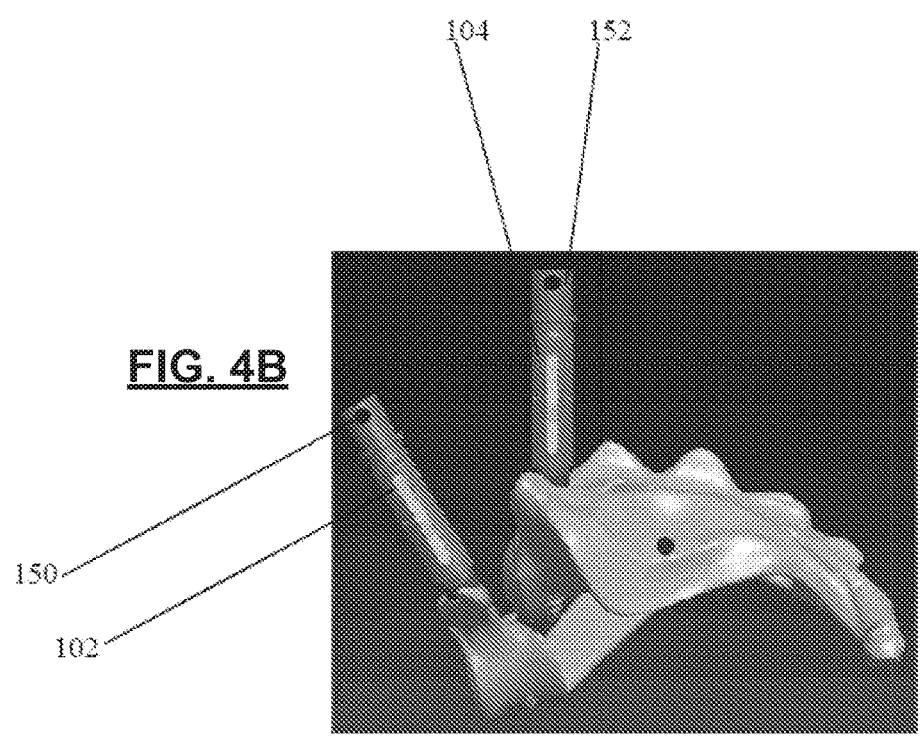

FIG. 4A illustrates an exemplary embodiment of the pedicle screws 10, 12 and towers 102, 104 being inserted into the chosen vertebrae. In FIG. 4A, pedicle screw 12 and tower 104 have already been installed, and the driver 80 is inserted within the tower 102 in order to install pedicle screw 10 and tower 102, using an MIS type technique. FIG. 4B shows both pedicle screws 10 and 12 installed in their respective vertebrae, with the driver 80 removed.

Figure 5:
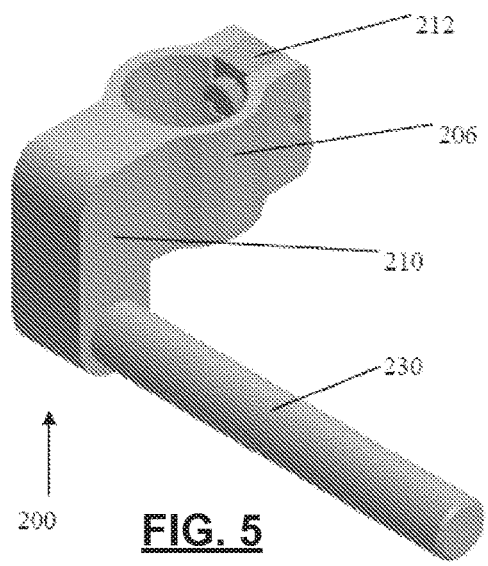
FIG. 5 is a perspective view of one embodiment of a first reduction assembly of the present invention.

Continuing now with FIG. 5, the first reduction assembly 200 is shown. The first reduction assembly 200 and tower 102 may include additional features that link to the second reduction assembly 300 and tower 104. Once linked, the second reduction assembly 300 may be used to apply forces on the first reduction assembly 200 to reposition the L5 vertebra. For example, the first reduction assembly 200 may include a load transfer ring 206, a body member 210, and a load transfer link member/rod 230. The transfer ring 206 may be coupled to the proximal end of the lumbar tower 102, such as by mating features 109 and/or quick-release engagement feature 150 and quick-release trigger 212. In one embodiment, the transfer ring 206 may rotate about a longitudinal axis of the lumbar tower 102. In one embodiment, the transfer ring 206 is fixedly coupled to the proximal end of the lumbar tower 102.

In one embodiment, the first reduction assembly 200 may further comprise a quick-release mechanism. A quick-release trigger 212 may be operably coupled to the load transfer ring 206 as to lock the proximal end of the tower assembly 102 in place. The quick-release trigger 212 may be rotatably coupled to the load transfer ring 206 of the first reduction assembly 200 by way of an opening, a pin, a spring, and/or similar means as known in the art. The quick-release trigger 212 may include a locking feature as to mate with the quick-release feature 150 on the proximal end of the first tower assemblies 102. The quick release trigger 212 and the load transfer ring 206 may secure the first reduction assembly 200 to the first tower assembly 102. The transfer link member/rod 230 may be fixedly coupled to a portion of the body member 210 of the first reduction assembly 200, and extend outward therefrom.

In an alternative embodiment (not shown), the first reduction assembly 200 may comprise load transfer link receiver (as discussed below in relation to the second reduction assembly 300) rather than the load transfer link member/rod 230.

The transfer link member/rod 230 extends away from the body member 210, a first end of the transfer link member/rod 230 disposed at the body member 210. A second end of the transfer link member/rod 230 may be configured to engage with the load transfer link receiver 360 of the second reduction assembly 300.

In an alternative embodiment, the transfer link member/rod 230 may further comprise means for distraction. In one embodiment, the means for distraction may comprise a ratcheted portion of the link member/rod 230, such that the link member/rod 230 includes stepped features as to mate with distraction features on the second reduction assembly 300. In one embodiment, the load transfer link receiver 360 may further comprise a distraction slide lock, distraction trigger, and distraction locking tube configured to operably engage with the link member/rod 230. Such distraction means is more fully discussed in commonly owned and co-pending application Ser. No. 13/835,938, incorporated herein by reference in its entirety. Similar means for distraction, as known in the art, may also be used.

Figure 6A:
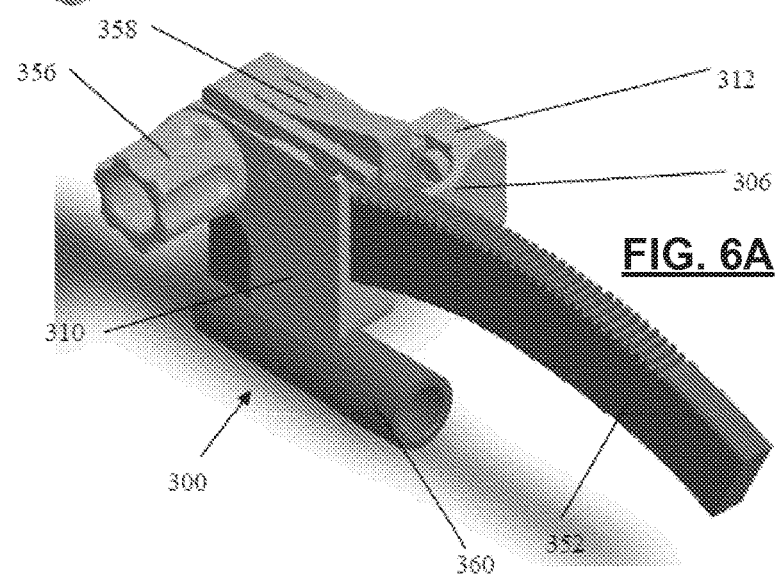
FIG. 6A is an isometric view of one embodiment of a second reduction assembly of the present invention.
Figure 6B:
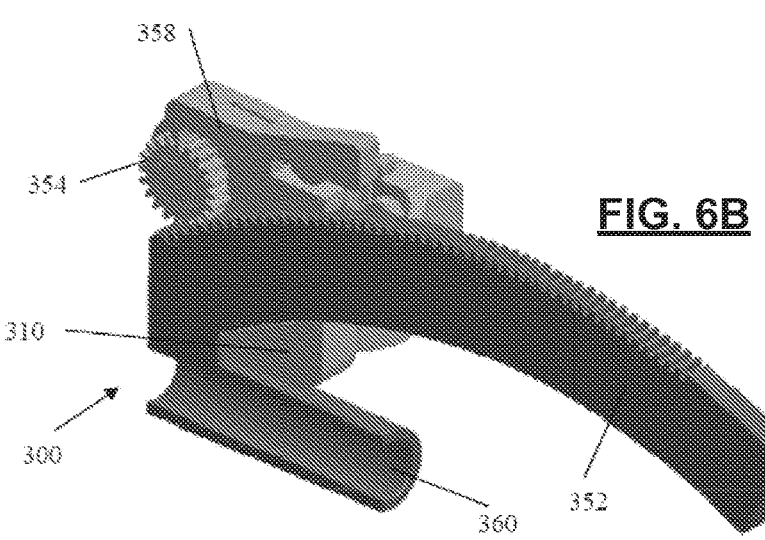
FIG. 6B is a cross-sectional view of FIG. 6A.

Referring to FIGS. 6A-B, the second reduction assembly 300 may include a load transfer ring 306 for mounting the second reduction assembly 300 on the proximal end of the second tower assembly 104. A quick-release trigger 312 may be operably coupled with the load transfer ring 306 as to lock the second reduction assembly 300 to the proximal end of the tower assembly 104. The quick-release trigger 312 may be rotatably coupled to the load transfer ring 306 of the second reduction assembly 300 by way of an opening, a pin, a spring, and/or similar means as known in the art. The quick-release trigger 312 may include a locking feature as to mate with the quick-release feature 152 on the proximal end of the second tower assemblies 104. The quick-release trigger 312 and the load transfer ring 306 may secure the second reduction assembly 300 to the second tower assembly 104. The second reduction assembly 300 may further comprise a reduction drive assembly 350. The reduction drive assembly 300 may be a rack and pinion type drive. In one embodiment, the reduction drive assembly 350 may comprise a body member 310, an arcuate or curved rack 352, a pinion 354 fixedly coupled to a knob 356, and a locking lever 358. The rack 352, pinion 354 and knob 356, and locking lever 358 are all operably and movably coupled to the body member 310. The rack 352 and body member 310 are configured such that the rack 352 may only translate in a single plane relative to the body member 310. The rack 352 may comprise any suitable arc or curvature to permit reduction in the vertical and horizontal directions simultaneously. The pinion 354 and knob 356 may be rotatably coupled to the body member 310, such as through one or more apertures in the body member 310.

In one embodiment, the pinion 354 includes a bore through which a shaft is disposed, the shaft being fixed to the knob 356. The bore and shaft may be configured to engage such that rotation of the knob 356 and rotation of the pinion 354 are coupled. The pinion 354 may comprise a round gear having a plurality of teeth configured to engage with a plurality of teeth 351 on the rack 352 such that rotational motion of the pinion 354 causes linear motion of the rack 352. In some embodiments, the pinion may comprise an alternative shape, so long as the pinion 354 is configured to engage the rack 352 and convert rotational force on the pinion 354 into lateral translation of the rack 352, as known in the art. The teeth of the rack 352 and pinion 354 may comprise any suitable configuration such that the translation of the rack 352 is controlled. The locking lever 358 may be operably coupled to the body member 310 and the pinion 354. In one embodiment, the locking lever 358 has a locking state and a released state, where the locking state is the default state of the locking lever 358. To release the locking lever 358, the lever 358 may be actuated so as to disengage the lever 358 from the pinion 354. In one embodiment, the locking lever 358 permits one-way rotation of the pinion 354, and must be released prior to reverse motion of the pinion 354. The reduction drive assembly 350 further comprises a load transfer link receiver 360. The receiver 360 may be fixedly coupled to the rack 352. As the rack 352 is advanced by rotation of the pinion 354, the receiver 360 is translated along the same arc as the rack 352.

In an alternative embodiment (not shown), the second reduction assembly 300 may comprise a load transfer link member/rod (as discussed above with regard to the first reduction assembly 200) rather than the receiver 360.

In an alternative embodiment, the load transfer link receiver 360 may further comprise means for distraction. In one embodiment, the means for distraction may comprise a distraction slide lock, a distraction trigger, and a locking tube. In one embodiment, the load transfer link/rod 230 may further comprise a ratcheted portion including stepped features as to mate with the distraction slide lock, trigger, and tube. Such distraction means is more fully discussed in commonly owned and co-pending application Ser. No. 13/835,938, incorporated herein by reference in its entirety. Similar means for distraction, as known in the art, may also be used.

Figure 14A:
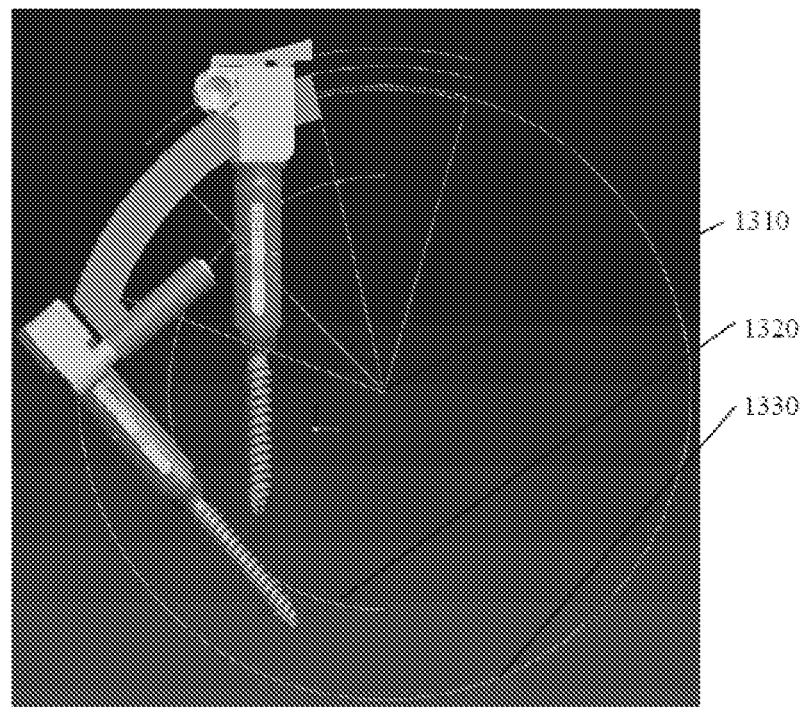
FIGS. 14A-14B show an exemplary curvature of the system of the present invention before reduction in retracted and extended states.
Figure 14B:
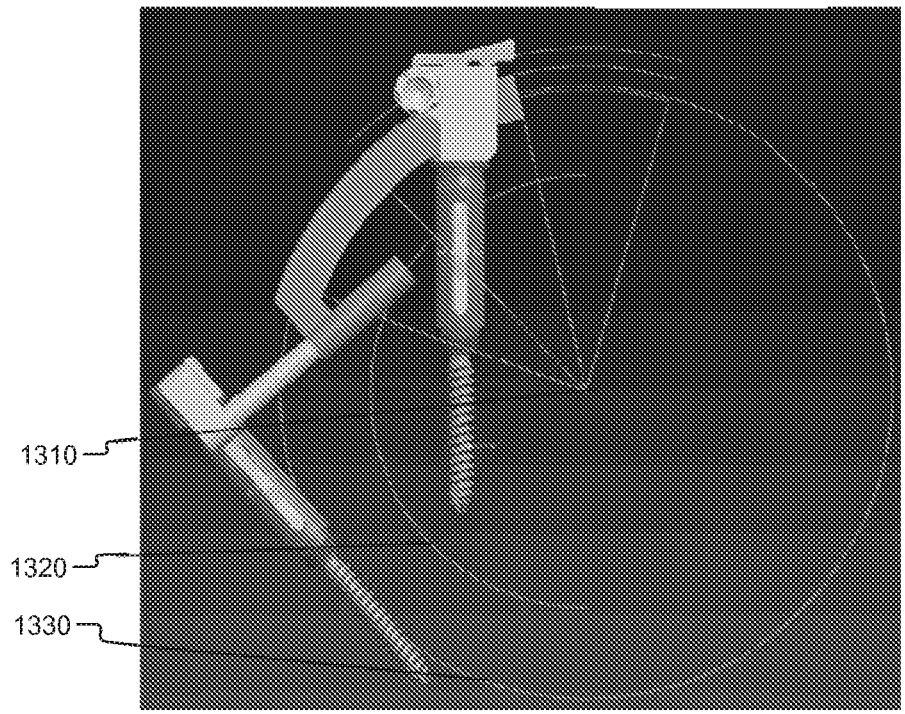
Figure 15A:
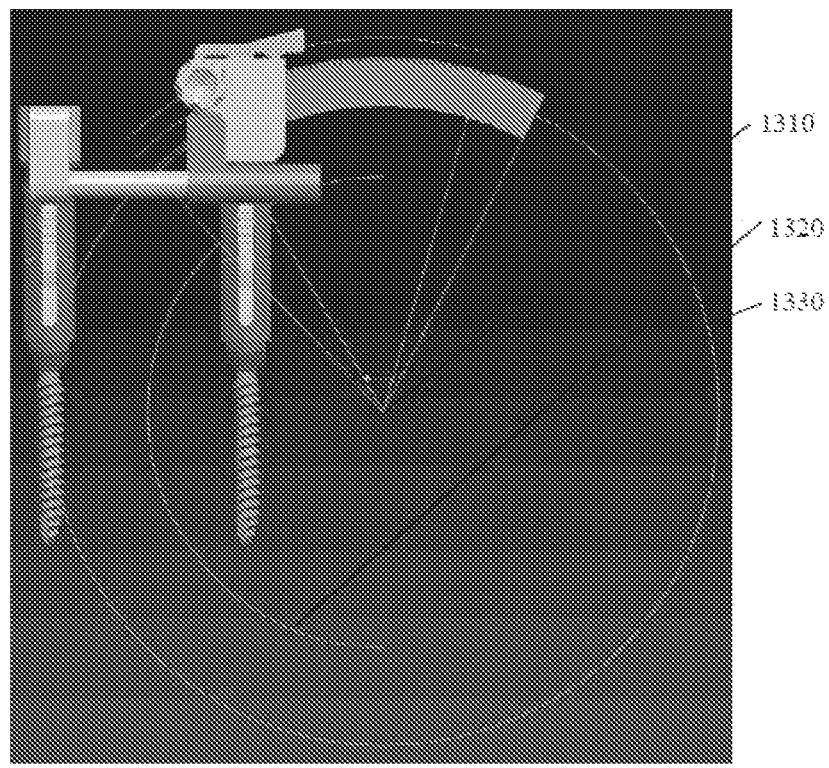
FIGS. 15A-15B show an exemplary state of the system of the present invention after reduction in extended and retracted states.
Figure 15B:
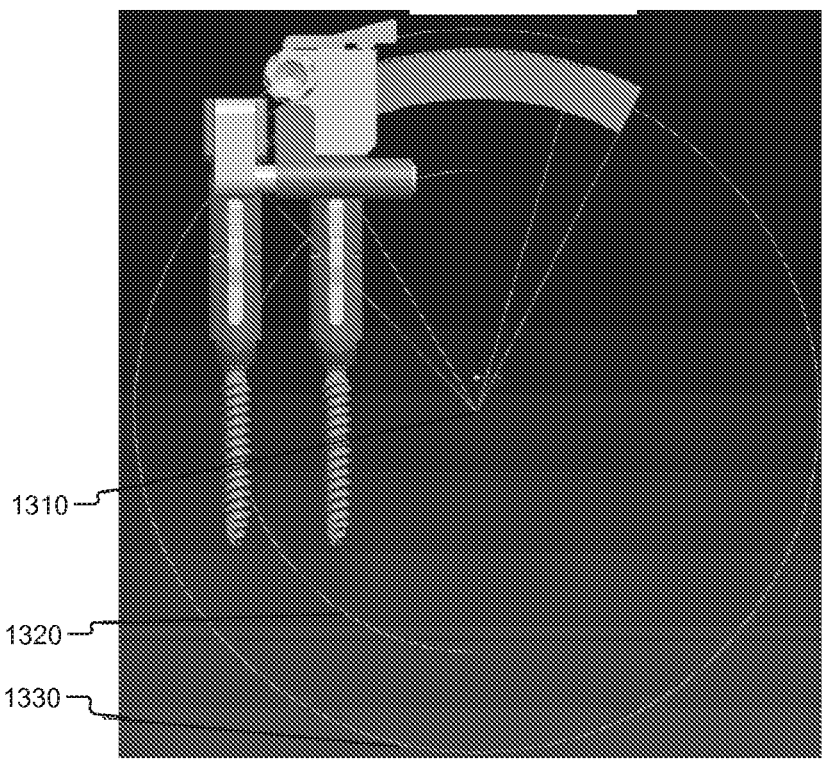
Figure 16A:
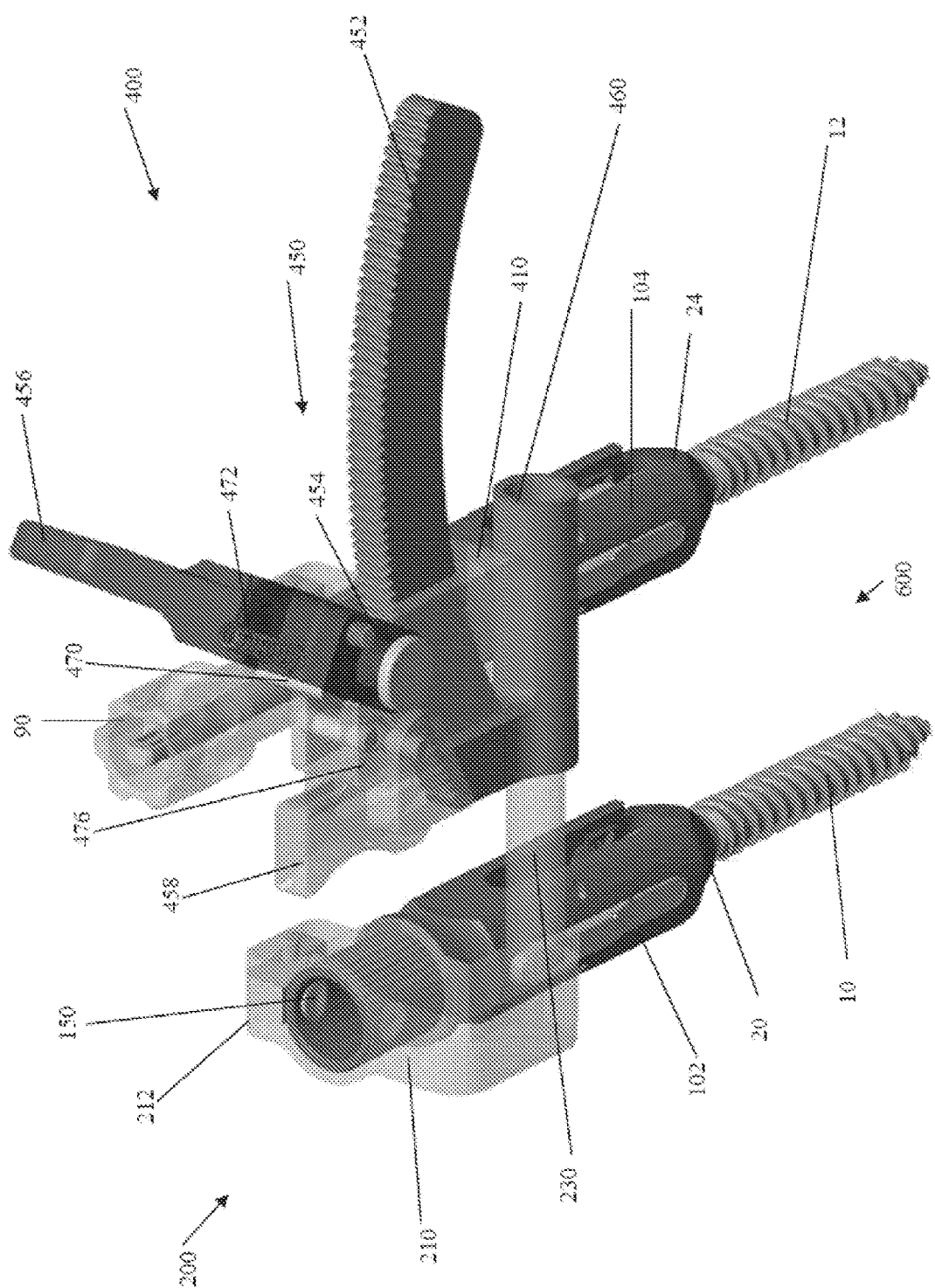
FIGS. 16A-16D show an alternative embodiment of the present invention, including a reduction lever in place of the knob.
Figure 16B:
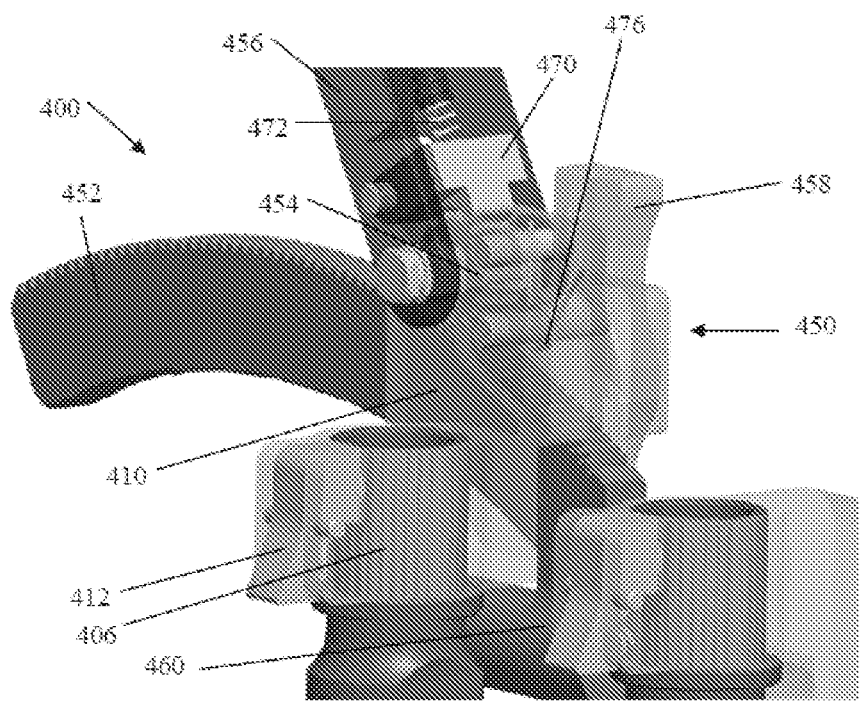
Figure 16C:
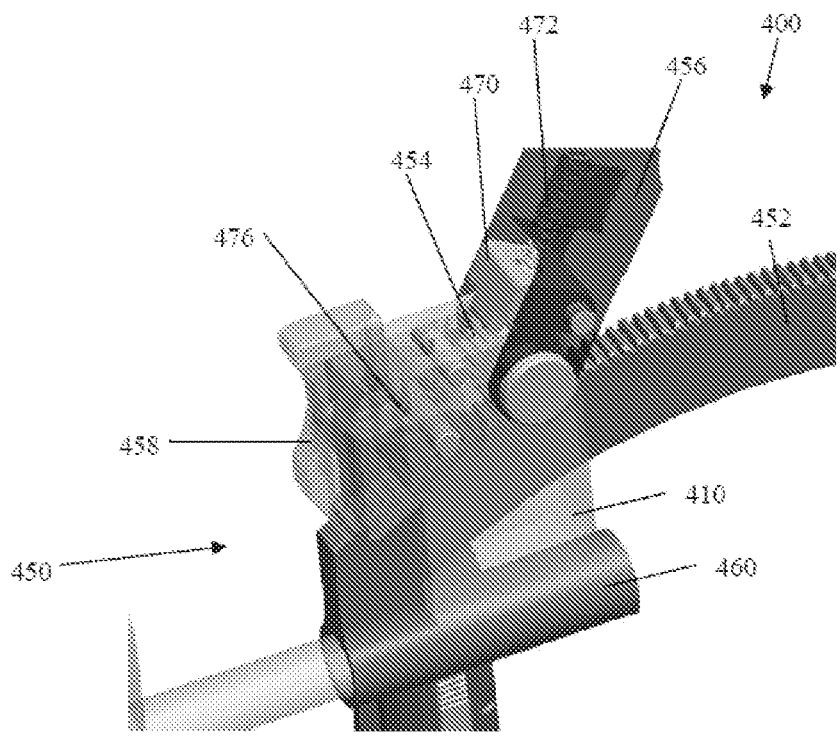
Figure 16D:
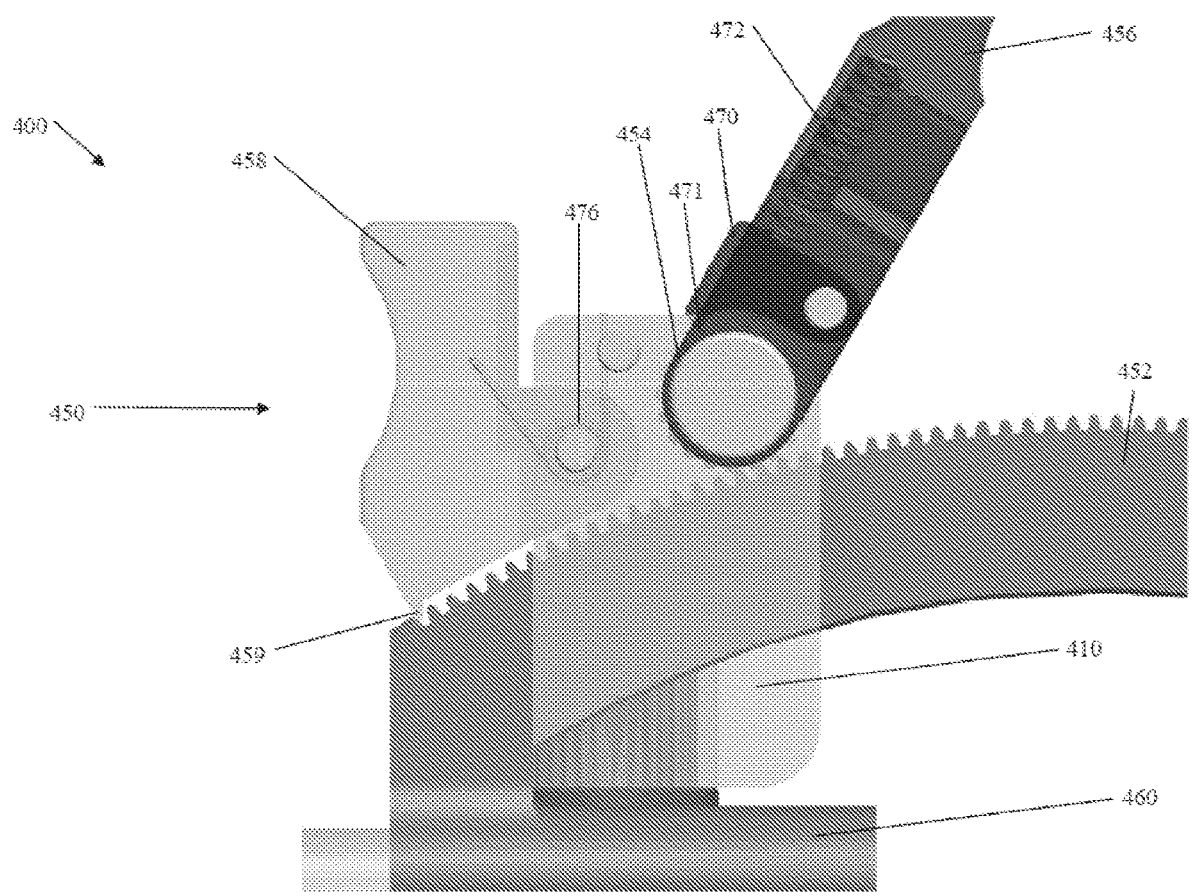

FIGS. 14A-B show the system 100 in an unreduced state where the load transfer link member/rod 230 can move freely during the reduction relative to the load transfer link receiver 360. The L5 vertebrae may be reduced into position by levering off of the placed screw 12 in the S1 vertebrae, and the reduced state of the system 100 is shown in FIGS. 15A-B. Distraction can be applied before (see FIG. 14B) or after (see FIG. 15A) reduction of the L5. In some embodiments, the system 100 may include features to hold the distraction in place before, during, or after reduction. In one embodiment, a distractor may be incorporated into the system 100, as discussed above. In another embodiment, a screw to screw distractor may be used to provide the distraction. In another embodiment, any means for distraction, as known in the art, may be used to provide the distraction, and/or incorporated into the system 100.

In one embodiment, the load transfer link member/rod 230 is freely movable relative to the load transfer link receiver 360. As such, the load transfer link member/rod 230 may be in an extended state (see FIGS. 14B and 15A) or a retracted state (see FIGS. 14A and 15B). Alternatively, the load transfer link member/rod 230 may be in a partially extended state between the extended state and the retracted state. Extension of the load transfer link member/rod 230 may allow the system 100 to accommodate different spacings depending on the position of the screws, vertebrae, etc. During reduction, the system 100 may rely on the surrounding tissues to hold the extended load transfer link member/rod 230 in position. The load transfer link member/rod 230 may be configured to have any length suitable for the particular procedure in which the system 100 is used.

FIGS. 7-12 illustrate the process of attaching and operating the system 100.

Figure 7A:
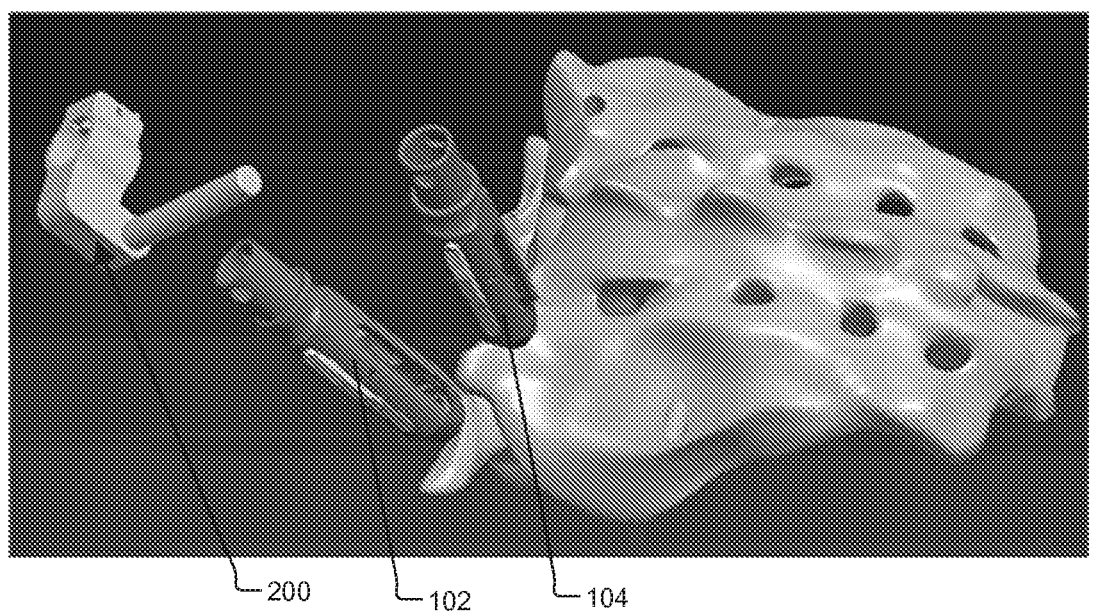
FIGS. 7A-7B illustrate the process of coupling the first reduction assembly to the first tower.
Figure 7B:
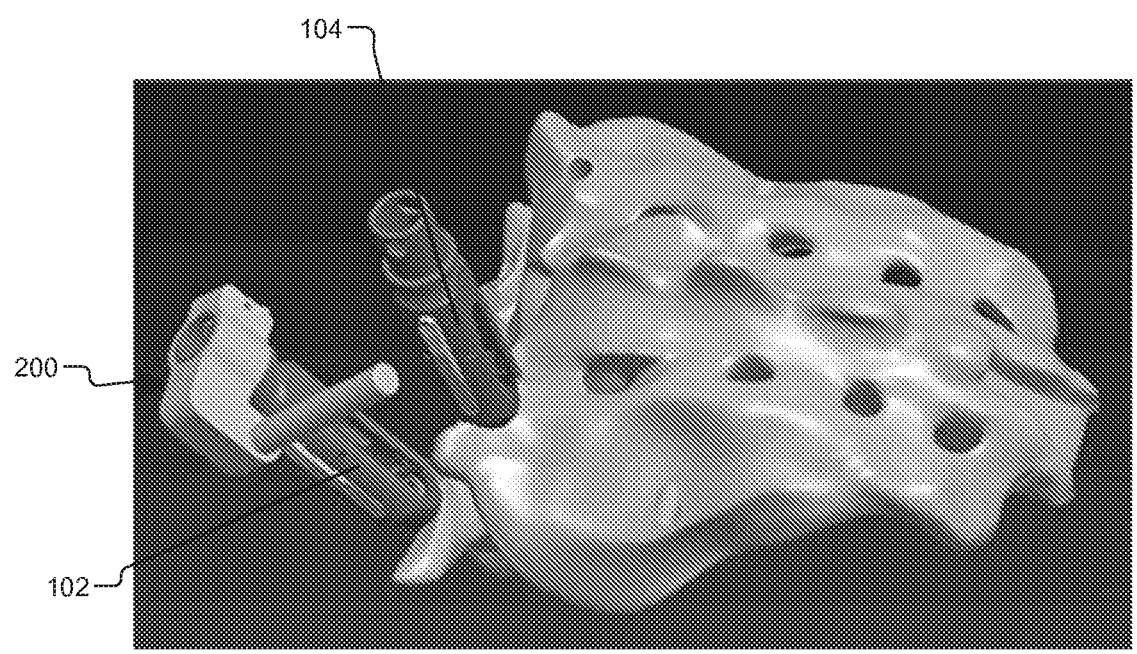

FIGS. 7A-B illustrate the process of coupling the first reduction assembly 200 to the first tower 102. In FIG. 7A, the first reduction assembly 200 is being placed onto the proximal end of the first tower 102, in the manner described above. FIG. 7B shows the first reduction assembly 200 after being coupled to the first tower 102.

Figure 8A:
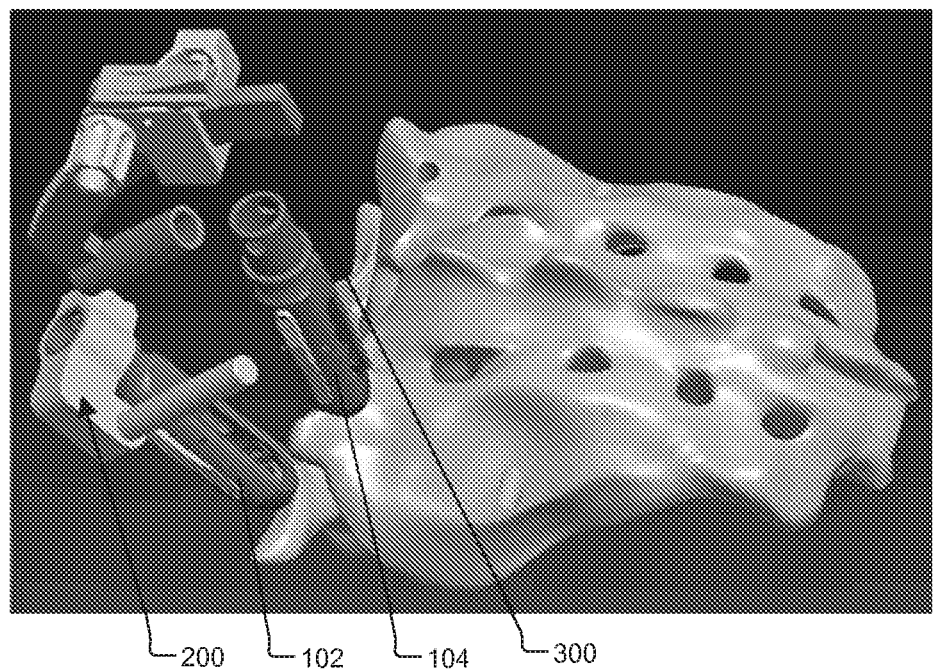
FIGS. 8A-8C illustrate the process of coupling the second reduction assembly to the second tower, and engaging the second reduction assembly with the first reduction assembly.
Figure 8B:
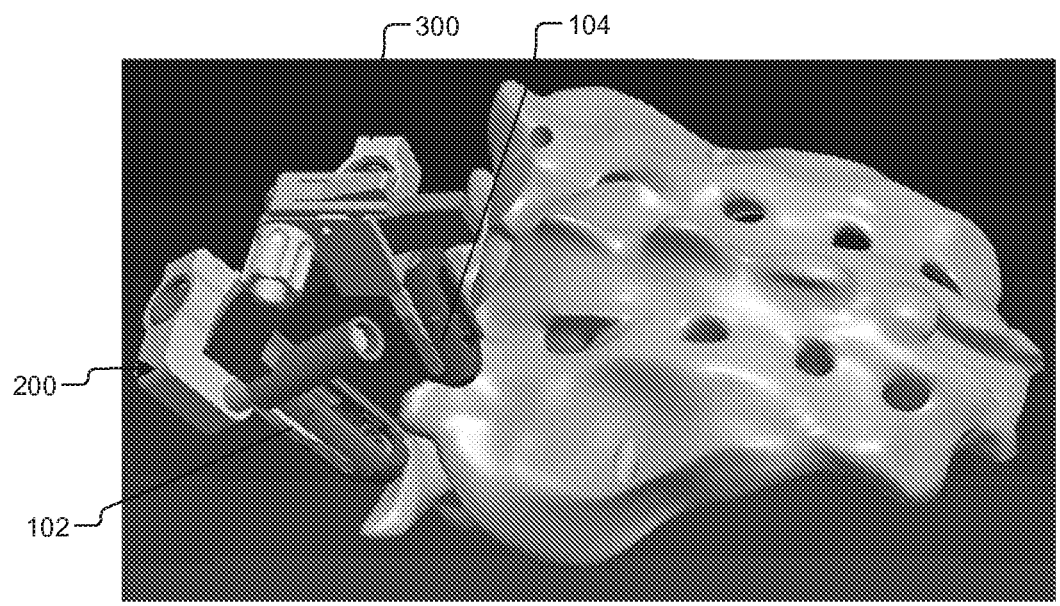
Figure 8C:
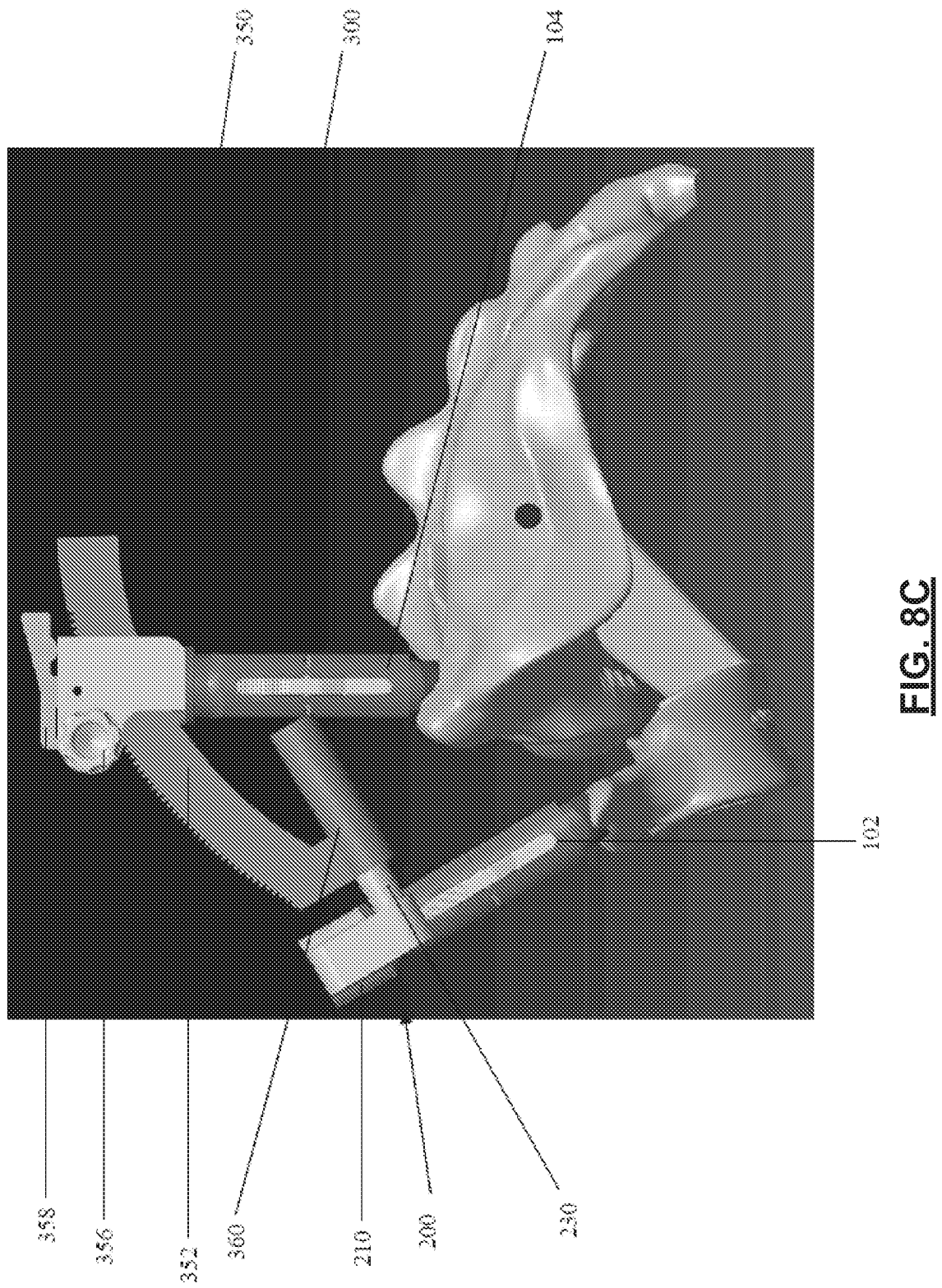

FIGS. 8A-C illustrate the process of coupling the second reduction assembly 300 to the second tower 104, and engaging the second reduction assembly 300 with the first reduction assembly 200. In FIG. 8A, the second reduction assembly 300 is being placed onto the proximal end of the second tower 104, in the manner described above. FIG. 8B shows the second reduction assembly 300 after being coupled to the second tower 104, and the load transfer link member/rod 230 engaging with the load transfer link receiver 360. FIG. 8C shows a side view of the embodiment of FIG. 8B, to highlight the displacement of the vertebrae.

Figure 9A:
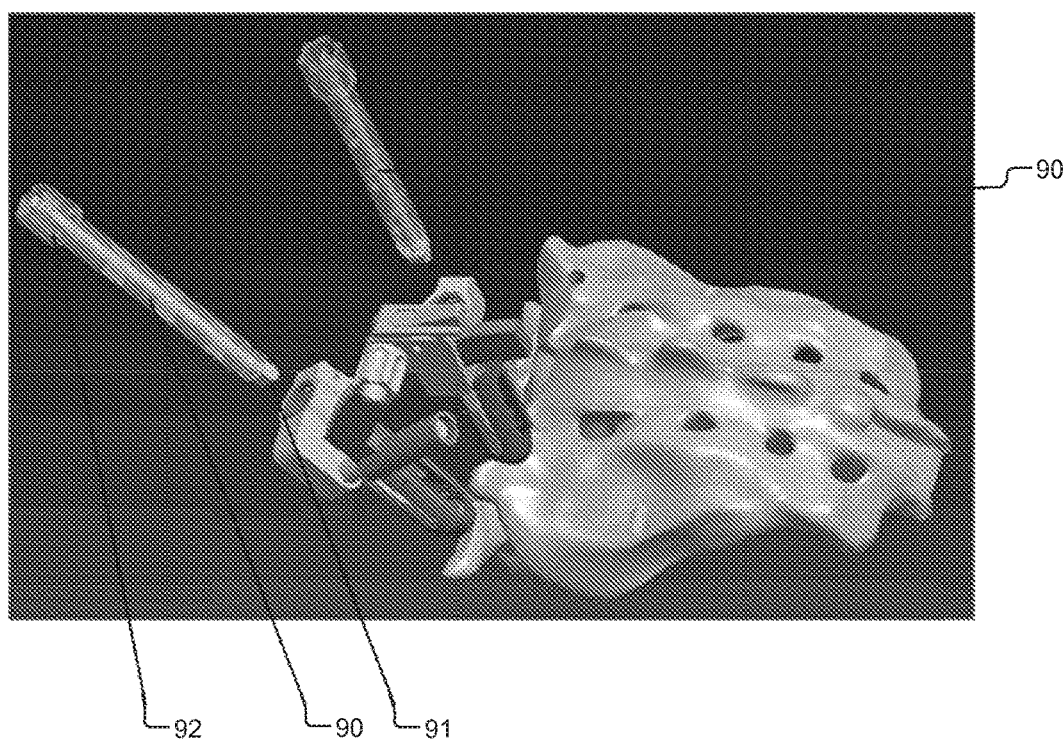
FIGS. 9A-9B illustrate the process of provisionally locking the polyaxial screws with provisional lockers, prior to reduction.
Figure 9B:
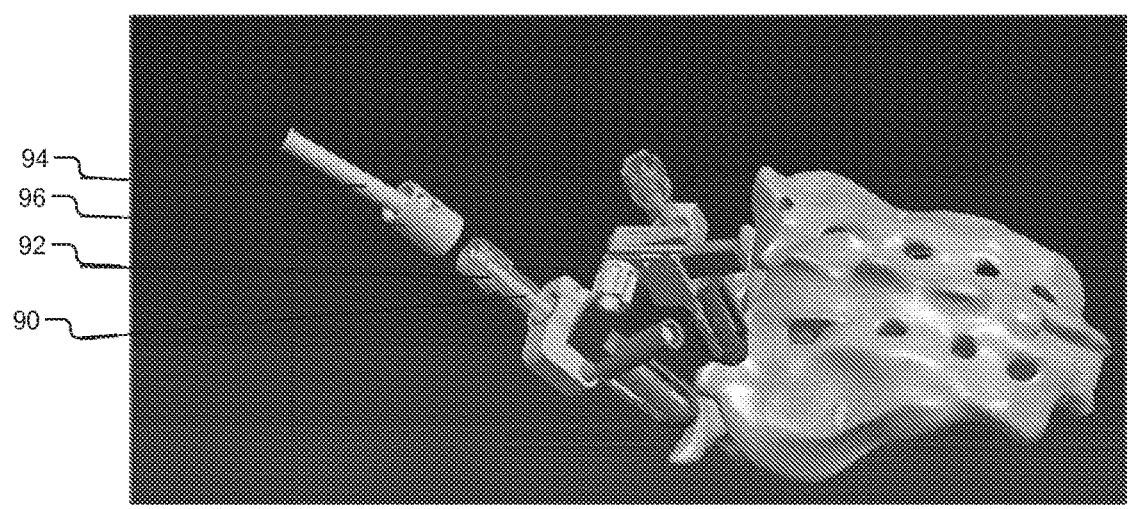

FIGS. 9A-B illustrate the process of provisionally locking the polyaxial screws with provisional lockers, prior to reduction. Prior to reduction, the pedicle screws 10, 12 may be provisionally locked to prevent slippage of the screw heads during reduction. Provisional lockers 90, each having distal engagement tip 91 and proximal head 92, may be used to provisionally lock the pedicle screws 10, 12. The lockers 90 may be disposed within the towers 102, 104 such that the engagement tips 91 engage the heads of the screws 10, 12. Once the tips 91 engage the heads of the screws 10, 12, the locker 90 may be rotated to provisionally lock the screw heads. In one embodiment, shown in FIG. 9B, a driver 94 may be used to rotate the lockers 90. The driver 94 may be configured so as to increase the torque that may be applied to rotate the lockers 90. The driver 94 may have a distal engagement member 96 that is configured to engage the heads 92 of the lockers 90. Once the screws 10, 12 are provisionally locked, reduction may begin.

Figure 10A:
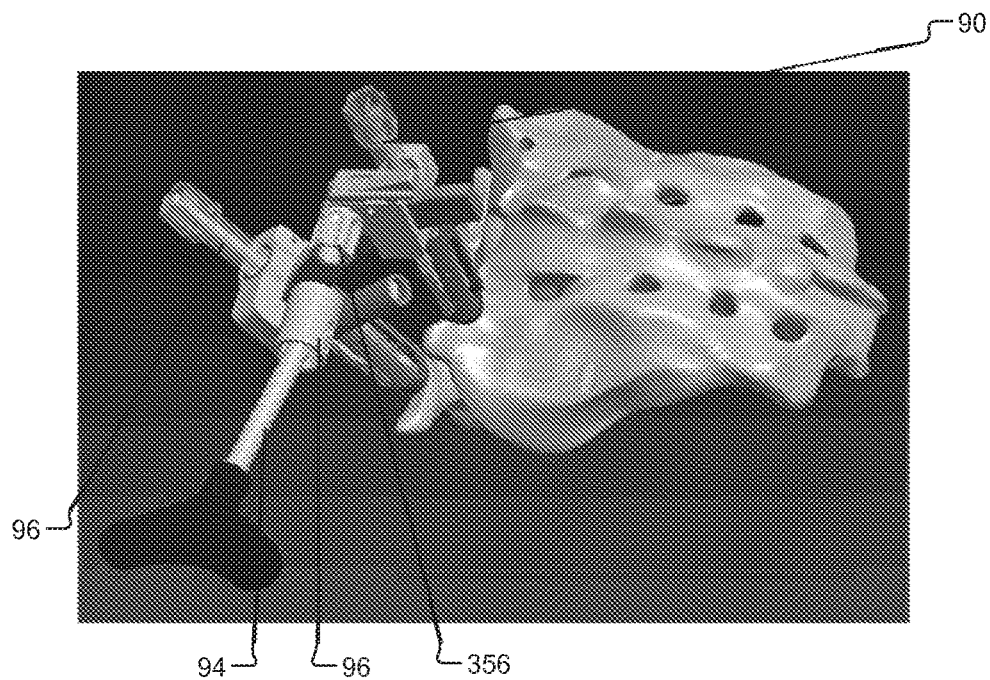
FIG. 10A is an isometric view of a driver being applied to a reduction driver assembly of the second reduction assembly.
Figure 10B:
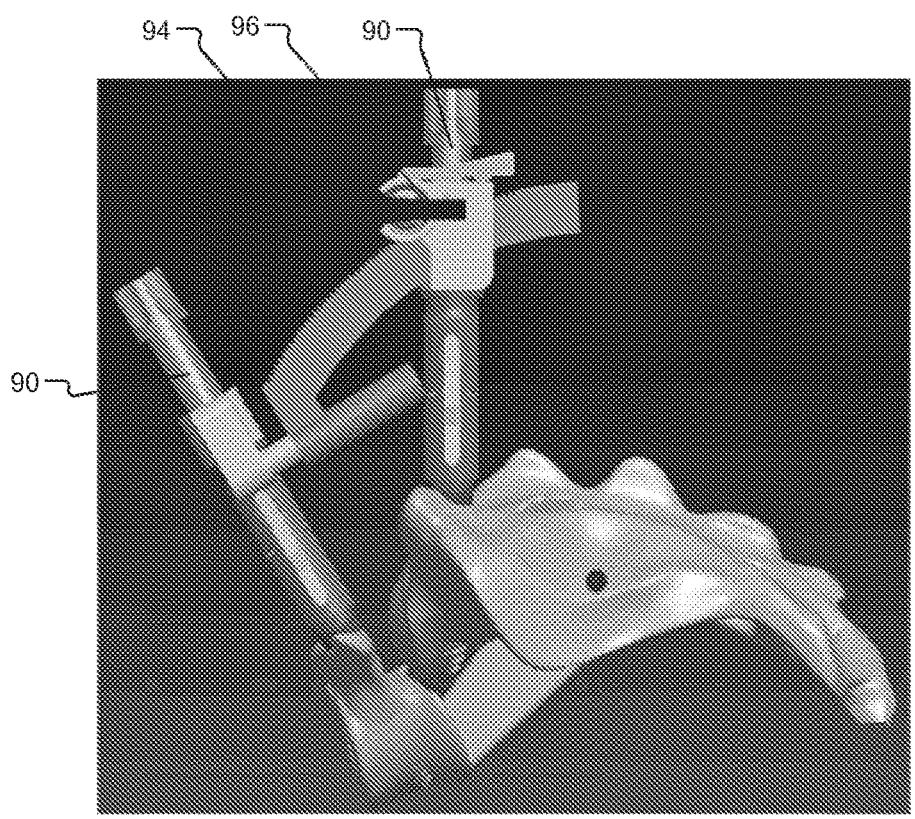
FIG. 10B is a side view of FIG. 10A.

To drive the reduction, the knob 356 may be rotated to translate the arcuate rack 352 by rotation of the pinion 354. As shown in FIGS. 10A-B, in one embodiment, the driver 94 discussed above may be used to provide increased torque on the knob 356 to drive the reduction. In one embodiment, the knob 356 is configured to couple with the engagement member 96 of the driver 94, such that rotation of the driver 94 rotates the knob 356.

Figure 13A:
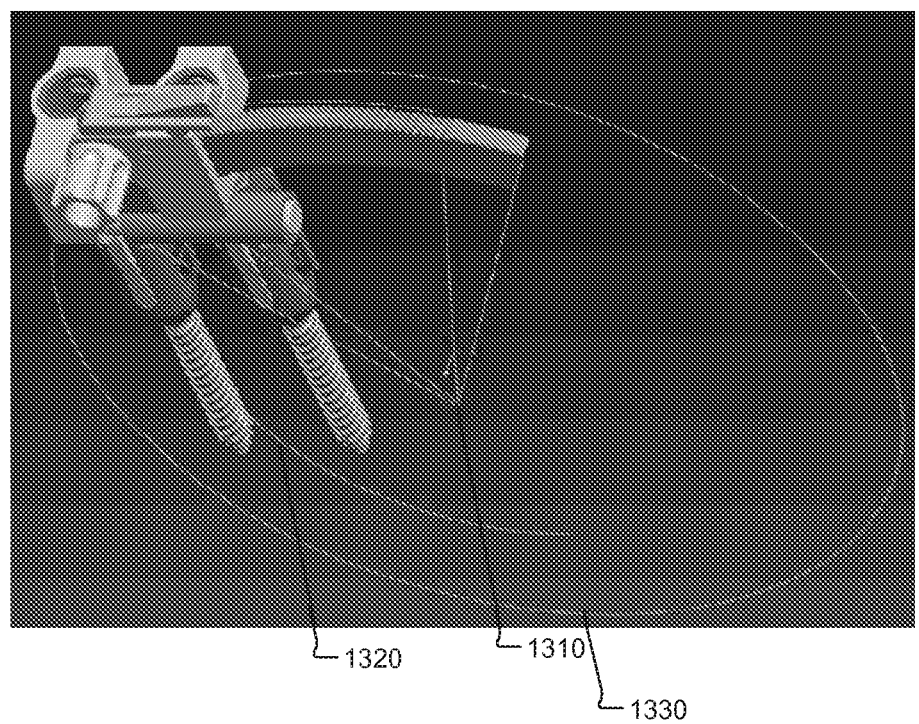
FIGS. 13A-13B show exemplary datum curves for the path of movement and centers of rotation of the system of the present invention.
Figure 13B:
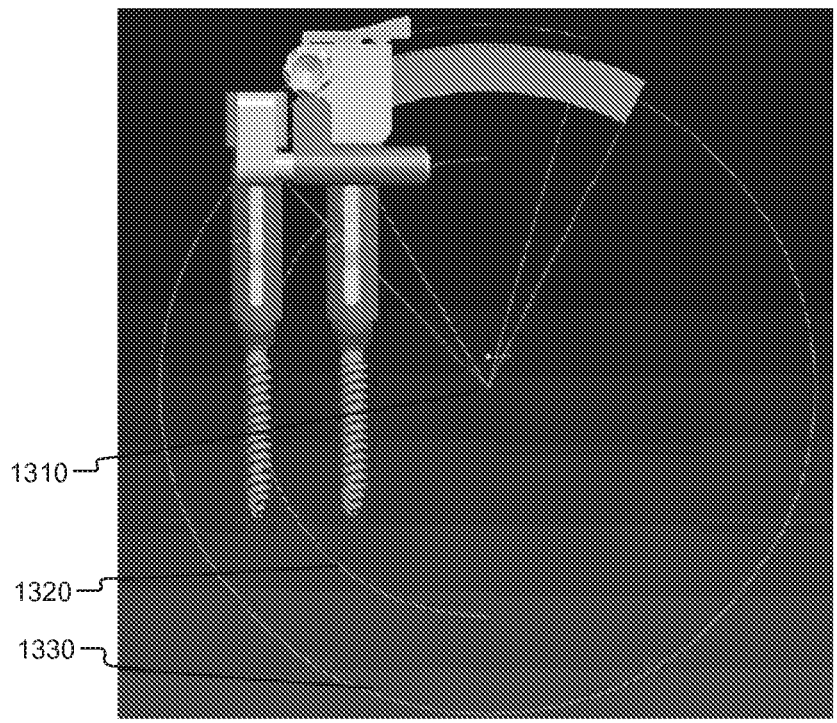

As the knob 356 is rotated, the rack 352 is drawn back, or "cammed." Exemplary depictions of the path of the rack 352 and screw 10 during reduction are shown in FIGS. 13-15.

Figure 11A:
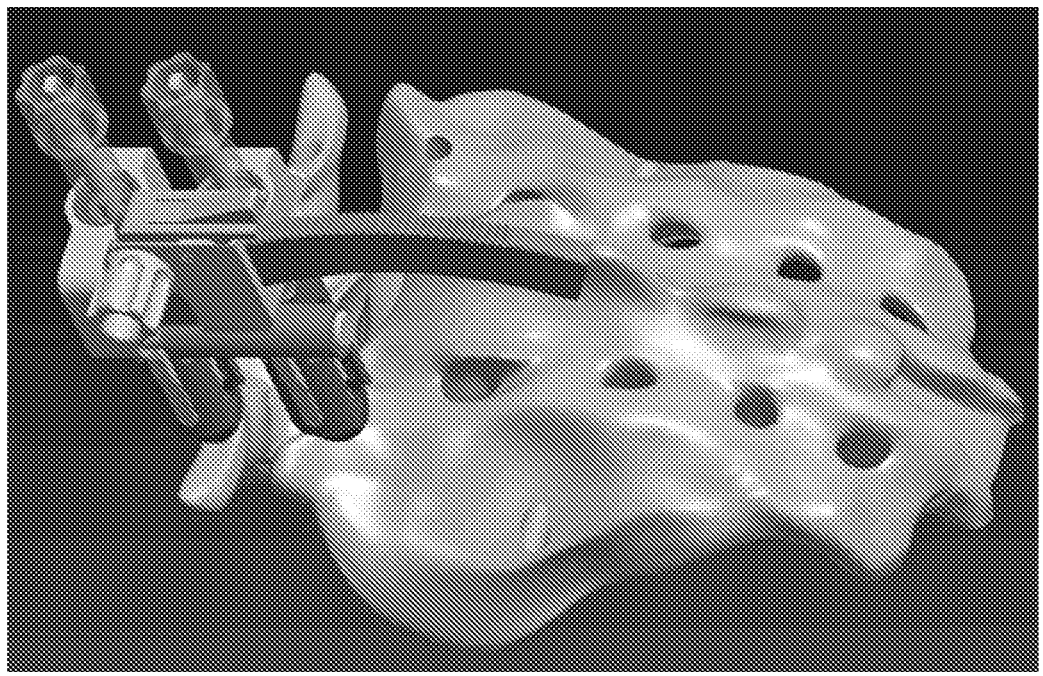
FIG. 11A is an isometric view of the installed system of the present invention, after reduction.
Figure 11B:
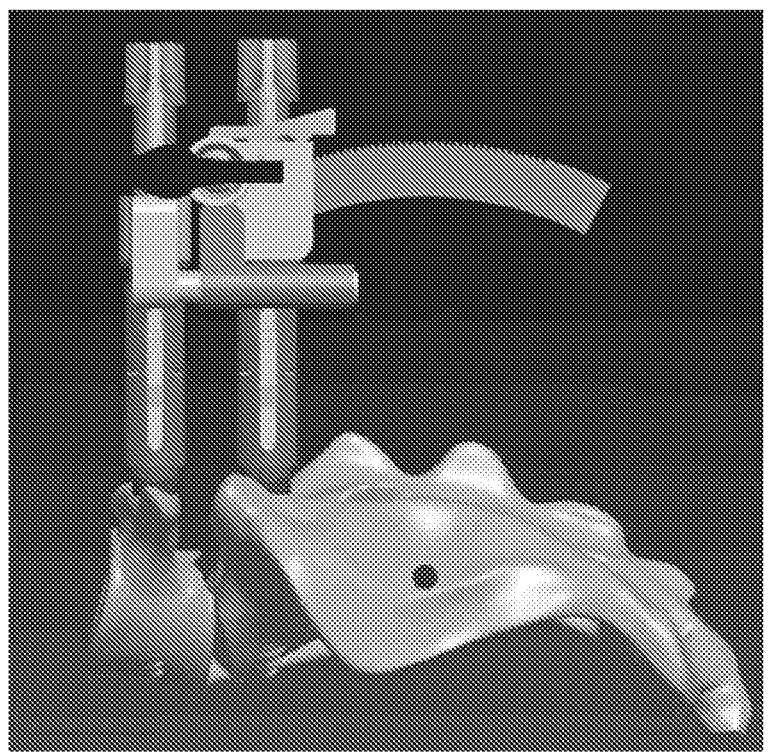
FIG. 11B is a side view of FIG. 11A.

FIGS. 11A-B show two views of the system 100 after reduction is completed, showing how the displaced vertebra is relocated by the reduction, as discussed above.

Figure 12:
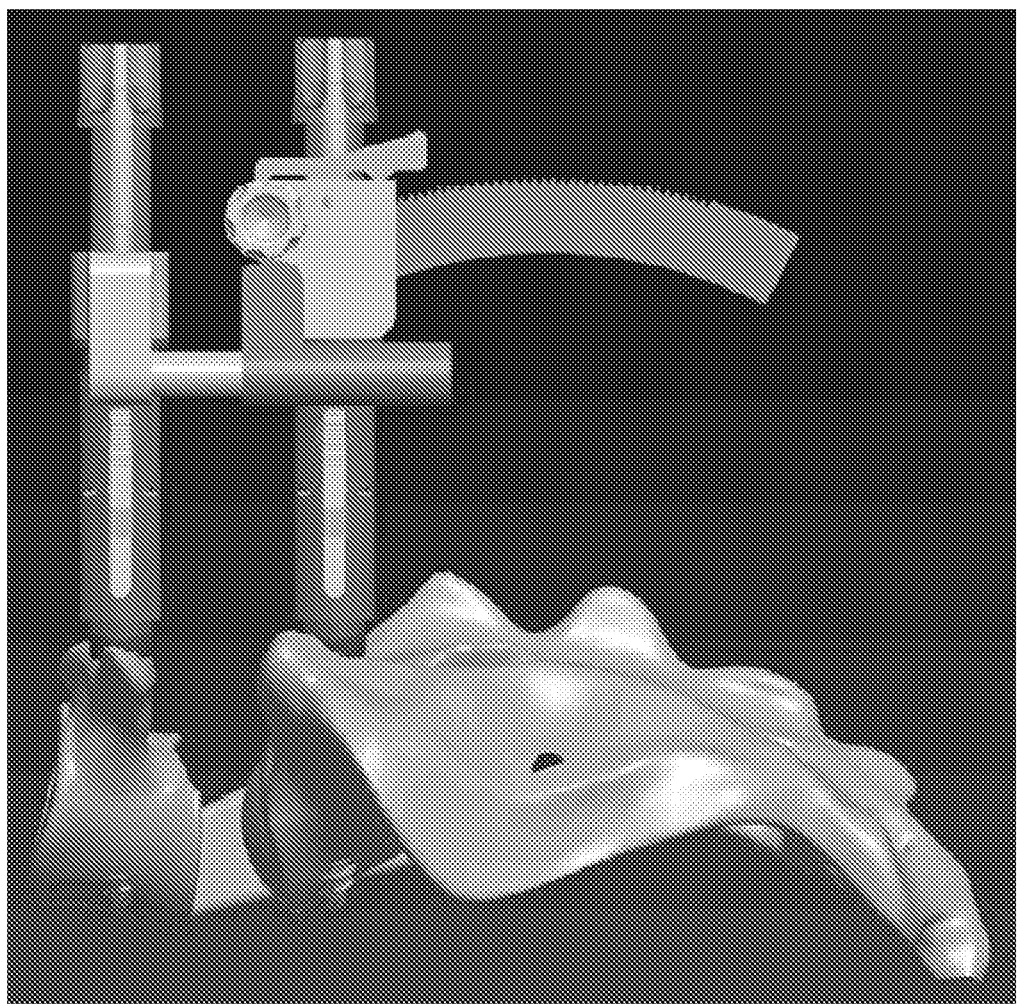
FIG. 12 is a side view of the installed system of the present invention, after reduction and distraction of the vertebrae.

FIG. 12 is a side view of the installed system 100 of the present invention, after reduction and distraction of the vertebrae, as discussed above.

In one embodiment, the system 100 may be used to correct spondylolisthesis at the L5-S1 level of the spine. For example, in FIGS. 2a-b, 4a-b, and 7-10, the L5 vertebra has slipped forward or anteriorly from the S1 level of the sacrum. The slippage may occur due to degeneration of disc material between the L5 and S1 levels. The slippage may occur from a fracture of degeneration of the vertebral body and/or from fracturing of the L5 vertebra. In some cases, bone growth may occur on an upper surface of the S1 level due to rubbing from the L5 vertebra. The system 100 may be used to reposition the L5 vertebra into proper alignment with the S1 level and hold the L5 and S1 levels in place while permanent fixation is added in the form of fixation rods and set screws.

The load transfer link member/rod 230 slidably engages with the transfer load link receiver 360 to permit free translational movement of the L5 vertebra in the sagittal plane. Movement of the L5 vertebra is accommodated by the arcuate translation of the rack 352 and the tower 102 and screw 10. As shown in FIGS. 11A-B, the knob 356 may be rotated and the rack 352 translated until the L5 level is brought into proper alignment with the S1 level. As the L5 level is positioned posteriorly, the sliding engagement of the load transfer link member/rod 230 with the transfer link receiver 360 allows the L5 vertebra to follow a path of least resistance. Once the vertebra L5 is properly aligned with the S1 level of the sacrum, rods (not shown) may be inserted into the receiving portions 20, 24 of the screws 10 and 12, as known in the art. Each tower assembly 102 and 104 may also be cannulated to permit insertion of setscrews within the receiving portions 20, 24 of the screws 10 and 12 to permanently secure the L5-S11 level. Additionally, a spacer or other interbody device may be secured between the L5 vertebra and 51 level of the sacrum. Bone material may be inserted with the spacer or interbody device to promote bone fusion and bone growth to permanently fuse the L5-S1 level.

In some embodiments, a distractor or distraction means may be applied after reduction is complete. The distractor or distraction means (not shown) may be used to increase the separation between the vertebrae as necessary for any further procedures or steps, as shown in FIG. 12.

FIGS. 13-15 show exemplary datum curves of the system 100 for the path of movement and centers of rotation. As shown, the center of rotation 1310 may be located behind and below the screw 12 of the second tower 104. In some embodiments, the center of rotation 1310 substantially centers on the dome of the sacrum so that the natural curve of the sacrum may be followed and cammed around. The path of the screw 10 during reduction is shown by curve 1320, which is the path the L5 screw 10 will follow during reduction (see 13a-b).

FIGS. 14A-B show exemplary datum curves of the system 100 before reduction in retracted (FIG. 14A) and extended (FIG. 14B) states. FIGS. 15A-B show exemplary datum curves of the system 100 after reduction in extended (FIG. 15A) and retracted (FIG. 15B) states.

An alternative embodiment of the device is shown in FIGS. 16A-D, where the device 600 may comprise a drive assembly 450 that uses a reduction lever 456 in place of the knob 356 to drive the pinion 454. In this embodiment, the second reduction assembly 400 is generally similar to the second reduction assembly 300. The reduction assembly 400 may include a load transfer ring 406 for mounting the second reduction assembly 400 on the proximal end of the second tower assembly 104.

A quick-release trigger 412 may be operably coupled with the load transfer ring 406 as to lock the second reduction assembly 400 to the proximal end of the tower assembly 104. The quick-release trigger 412 may be rotatably coupled to the load transfer ring 406 of the second reduction assembly 400 by way of an opening, a pin, a spring, and/or similar means as known in the art. The quick-release trigger 412 may include a locking feature as to mate with the quick-release feature 152 on the proximal end of the second tower assemblies 104. The quick-release trigger 412 and the load transfer ring 406 may secure the second reduction assembly 400 to the second tower assembly 104.

The second reduction assembly 400 may further comprise a reduction drive assembly 450. The reduction drive assembly 400 may be a rack and pinion type drive. In one embodiment, the reduction drive assembly 450 may comprise a body member 410, an arcuate or curved rack 452, a pinion 454 coupled to a reduction lever 456, and a locking pawl 458. The rack 452, pinion 454 and lever 456, and locking pawl 458 are all operably and movably coupled to the body member 410. The rack 452 and body member 410 are configured such that the rack 452 may only translate in a single plane relative to the body member 410. The rack 452 may comprise any suitable arc or curvature to permit reduction in the vertical and horizontal directions simultaneously. The pinion 454 and reduction lever 456 may be rotatably coupled to the body member 410, such as through one or more apertures in the body member 410.

In one embodiment, the pinion 454 includes a bore through which a shaft is disposed, the shaft being fixed to the lever 456. The bore and shaft may be configured to engage such that movement of the lever 456 and rotation of the pinion 454 are coupled. The pinion 454 may comprise a round gear having a plurality of teeth configured to engage with a plurality of teeth on the rack 452 such that rotational motion of the pinion 454 causes linear motion of the rack 452. In some embodiments, the pinion 454 may comprise an alternative shape, so long as the pinion 454 is configured to engage the rack 452 and convert rotational force on the pinion 454 into lateral translation of the rack 452, as known in the art. The teeth of the rack 452 and pinion 454 may comprise any suitable configuration such that the translation of the rack 452 is controlled.

In some embodiments, the reduction lever 456 may further comprise a reduction pawl 470. The reduction pawl 470 may be configured to operably couple the reduction lever 456 and pinion 454 such that actuation of the lever 456 moves the pinion 454 in a single direction. A locking ridge 471 may be disposed on the reduction pawl 470, such that the locking ridge 471 is configured to engage the pinion 454 and permit one way translation of the lever 456 relative to the pinion 454. In use, the ridge 471 will freely permit the lever 456 to actuate in one direction to "load" the lever 456. As the lever 456 is actuated in the opposite direction, the ridge 471 will engage the pinion 454 and cause the pinion 4 to rotate with the lever 456, advancing the rack 452. A spring 472 may be used to provide tension on the reduction pawl 470.

The locking pawl 458 may be operably coupled to the body member 410 and the rack 452. In one embodiment, the locking pawl 458 has a locking state and a released state, where the locking state is the default state of the locking pawl 458. To release the locking pawl 458, the pawl 458 may be actuated so as to disengage the pawl 458 from the rack 452. In one embodiment, the locking pawl 458 permits one-way translation of the rack 452, and must be released prior to reverse motion of the rack 452. A locking ridge 459 may be disposed on the locking pawl 458, such that the ridge 459 is configured to engage the rack 452. The ridge 459 may be configured such that the rack 452 may advance in a single direction without release of the pawl 458. A torsion spring 476 may be operably coupled to the pawl 458 and the body 410.

Figure 18:
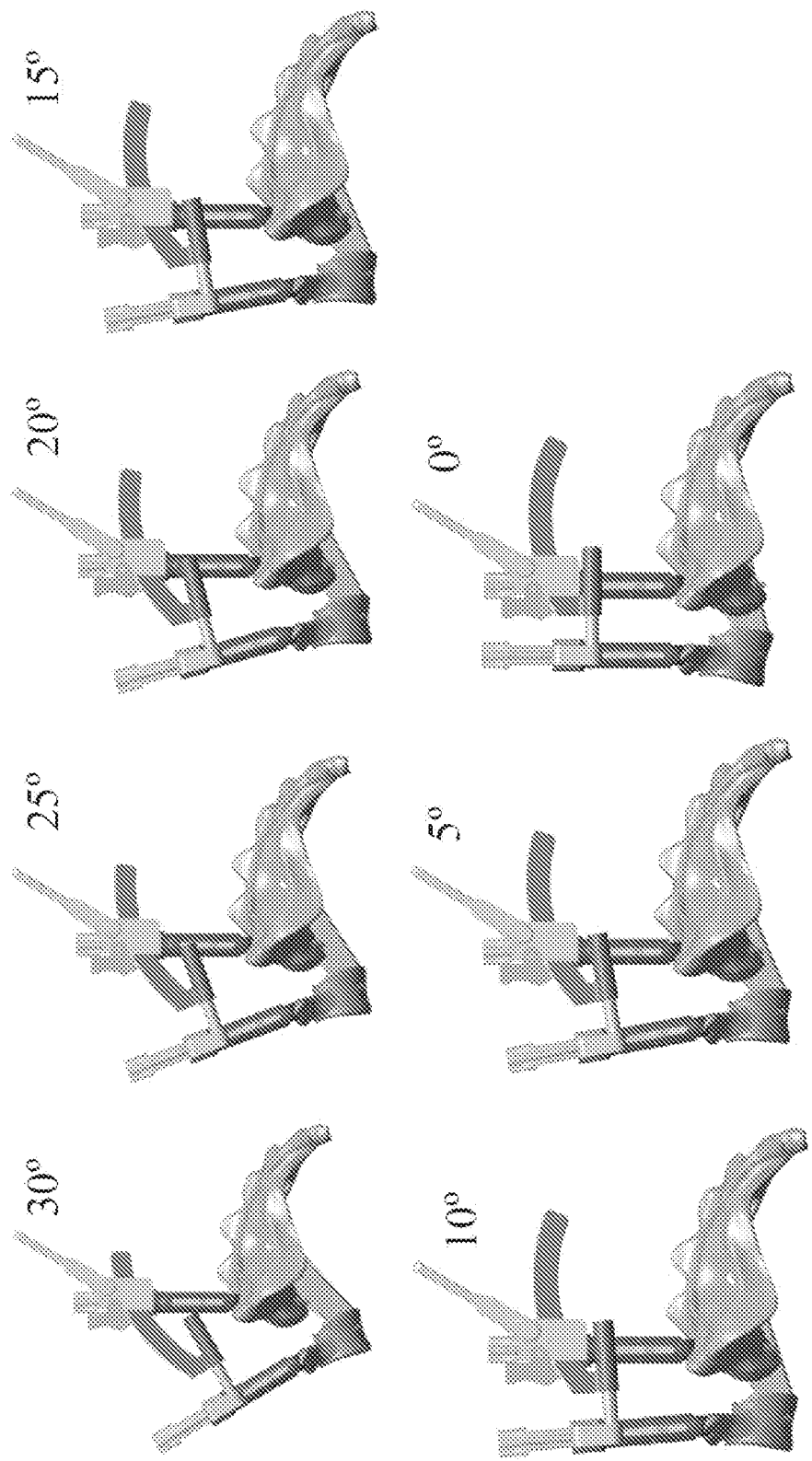
FIG. 18 illustrates the stages of reduction using the alternative embodiment of FIGS. 16A-16D.
Figure 19A:
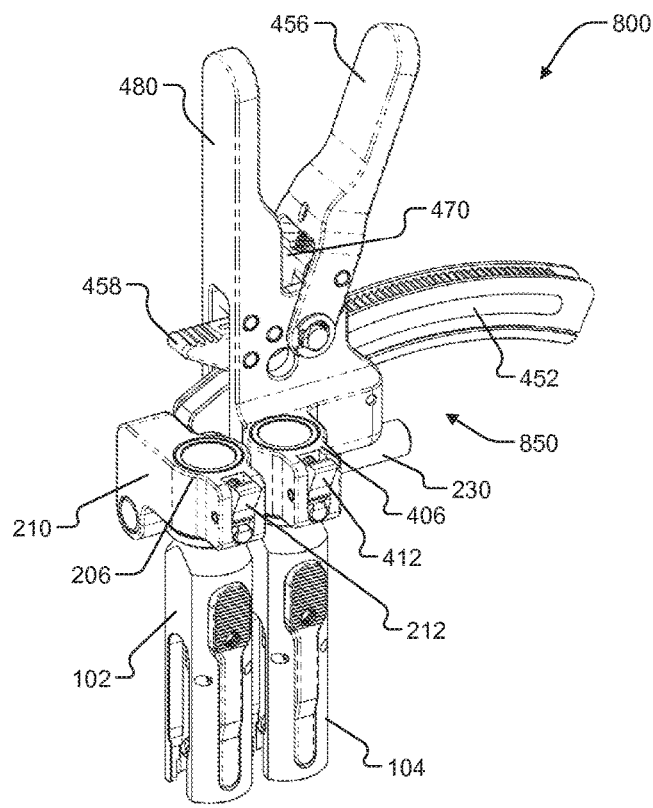
FIGS. 19A and 19B illustrate perspective views of an exemplary system for reduction of a spinal deformity coupled with first and second reduction towers.
Figure 19B:
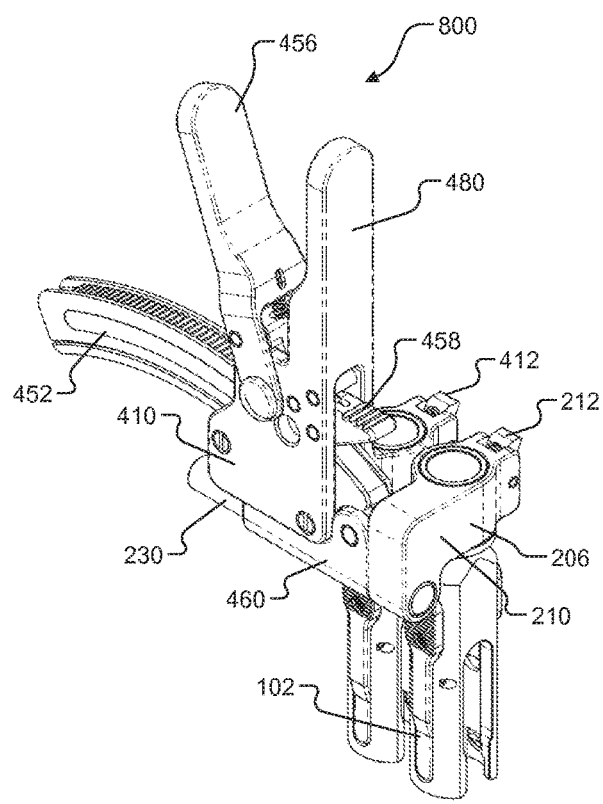
Figure 20:
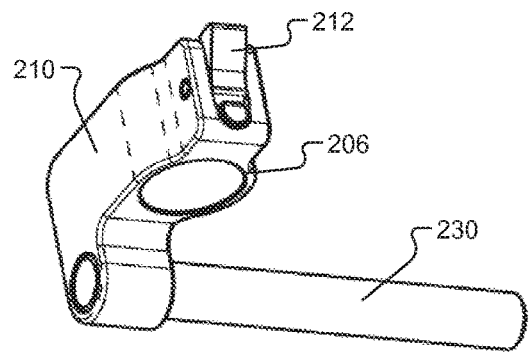
FIG. 20 is a perspective view of a first reduction assembly.
Figure 21:
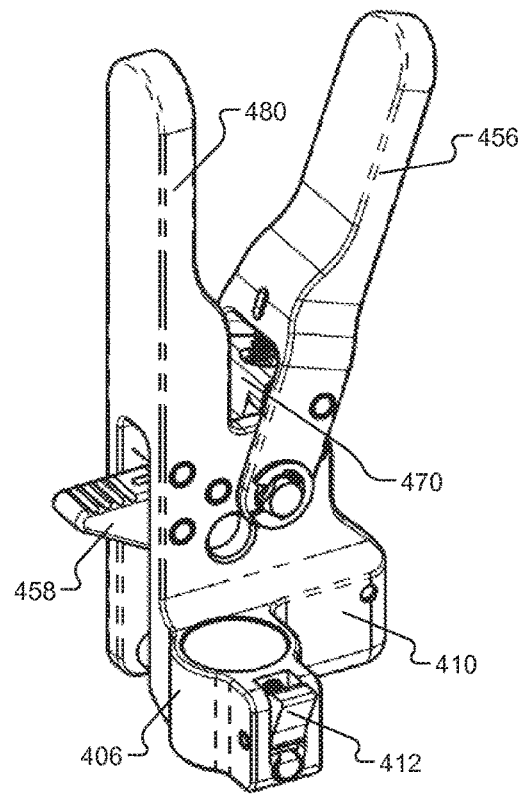
FIG. 21 is a perspective view of a second reduction assembly.

Together, the reduction pawl 470 and locking pawl 458 operate to permit a ratchet-like functionality to the reduction drive assembly 450. One of the reduction pawl 470 and locking pawl 458 is engaged with either the pinion 454 or rack 452 in each direction of motion. As the lever 456 is being "loaded," the locking pawl 458 engages the rack 452 to prevent slippage of the reduction drive assembly 450, while the reduction pawl 470 permits the lever 456 to freely rotate relative to the pinion 454. As the lever 456 is actuated to impart reduction, the locking pawl 458 permits the rack 452 to freely translate relative to the locking pawl 458, while the reduction pawl 470 engages the pinion 454 and causes the pinion 454 to rotate as the lever 456 is actuated. In this manner, the reduction drive assembly 450 may easily be operated through a plurality of stages of partial reduction, as illustrated in FIG. 18.

The reduction drive assembly 450 further comprises a load transfer link receiver 460. The receiver 460 may be fixedly coupled to the rack 452. As the rack 452 is advanced by rotation of the pinion 454, the receiver 460 is translated along the same arc as the rack 452.

In an alternative embodiment (not shown), the second reduction assembly 400 may comprise a load transfer link member/rod (as discussed above with regard to the first reduction assembly 200) rather than the receiver 460.

Figure 17A:
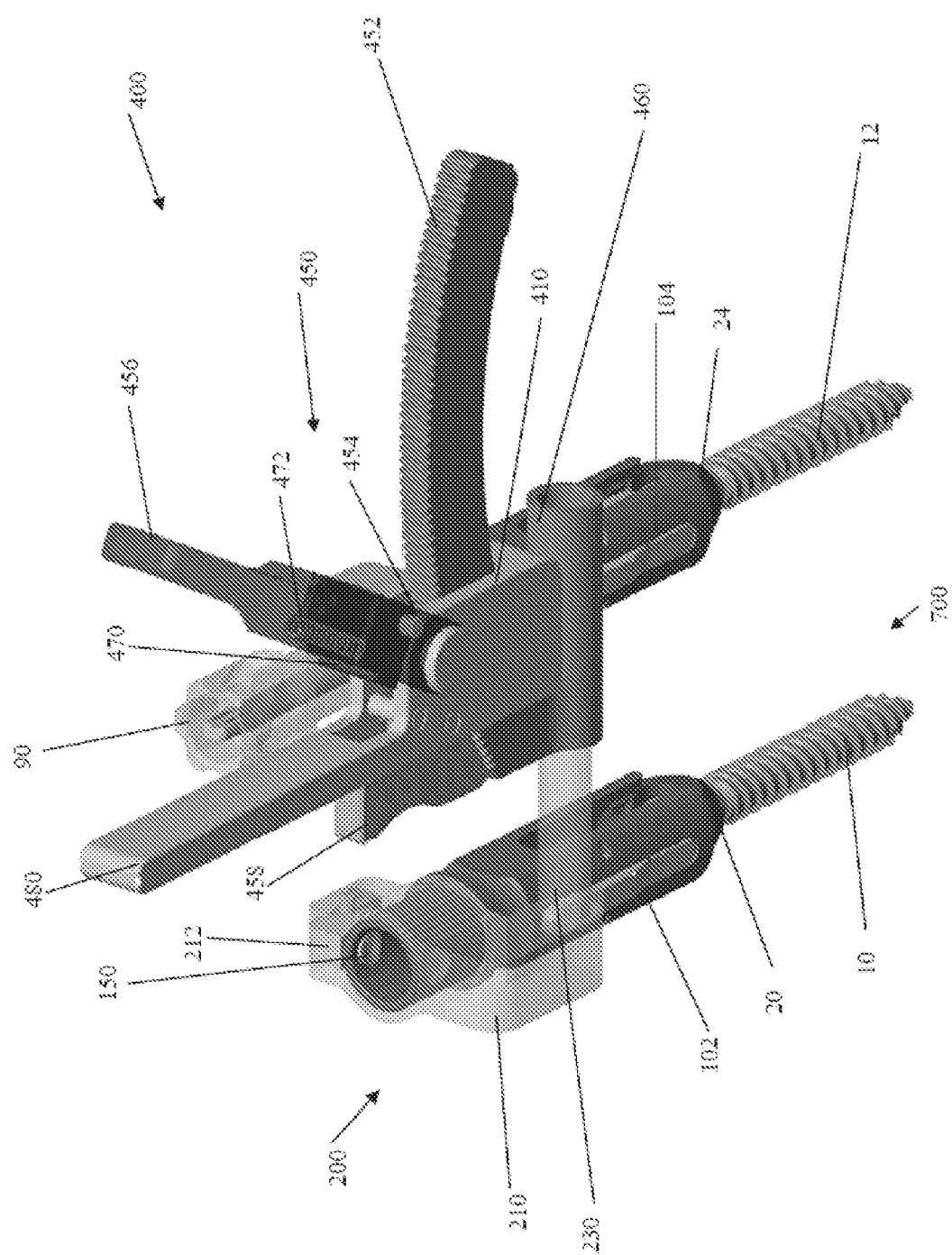
FIGS. 17A-17B show an alternative embodiment of the device of FIGS. 16A-16D, including a reduction handle member.
Figure 17B:
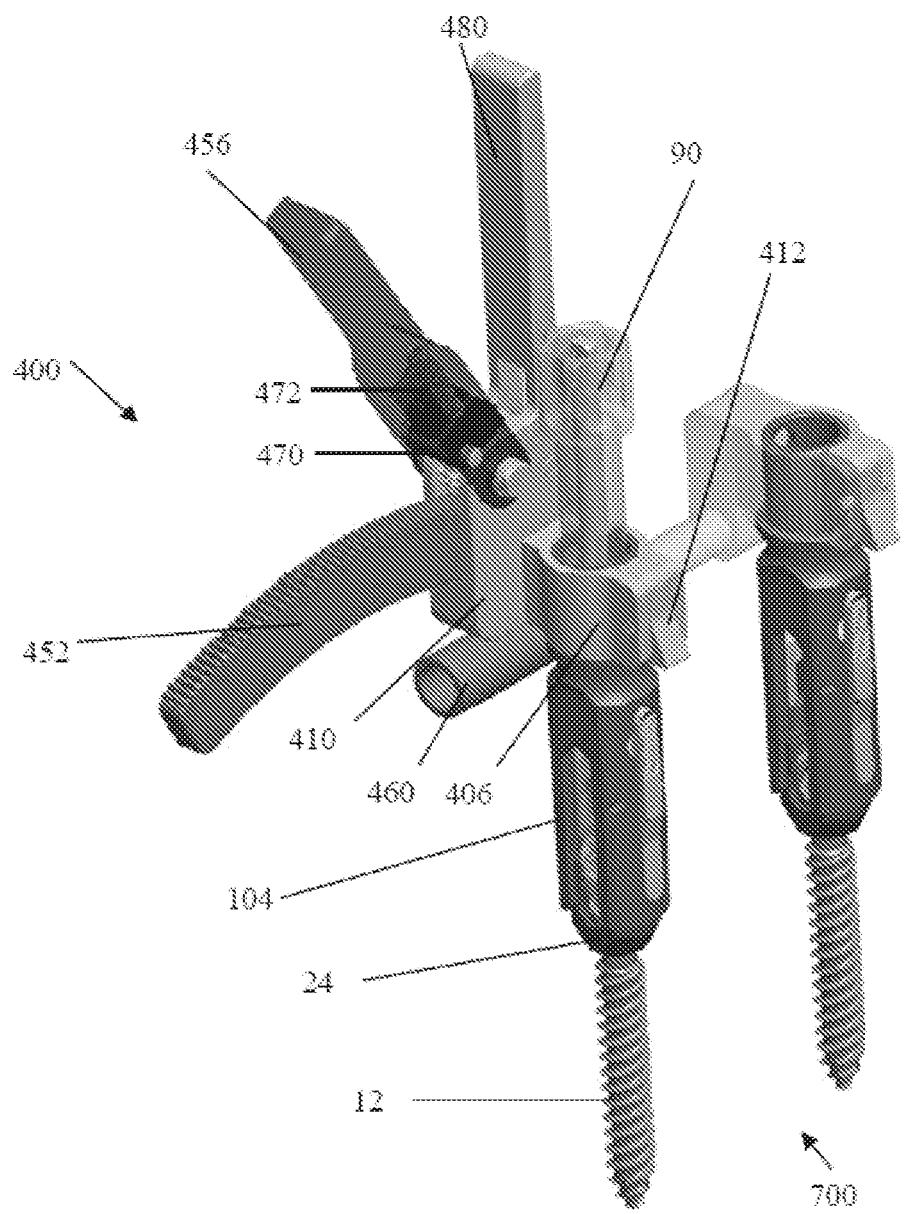

FIGS. 17A-B show an alternative embodiment of the device illustrated in FIGS. 16A-D. The device 700 is generally identical to the device 600 of FIGS. 16A-D, but the reduction drive assembly 450 may further comprise a reduction handle member 480. The reduction handle member 480 provides a grip point to assist in actuation of the reduction lever 456. In one embodiment, the reduction handle member 480 may comprise a generally rectangular projection from the body member 410 of the reduction drive assembly 450. In some embodiments, the reduction handle member 480 may comprise an alternative shape, as known in the art, including but not limited to: a curved handle, a handle with finger grips, cylindrical, and/or the like.

Figure 28:
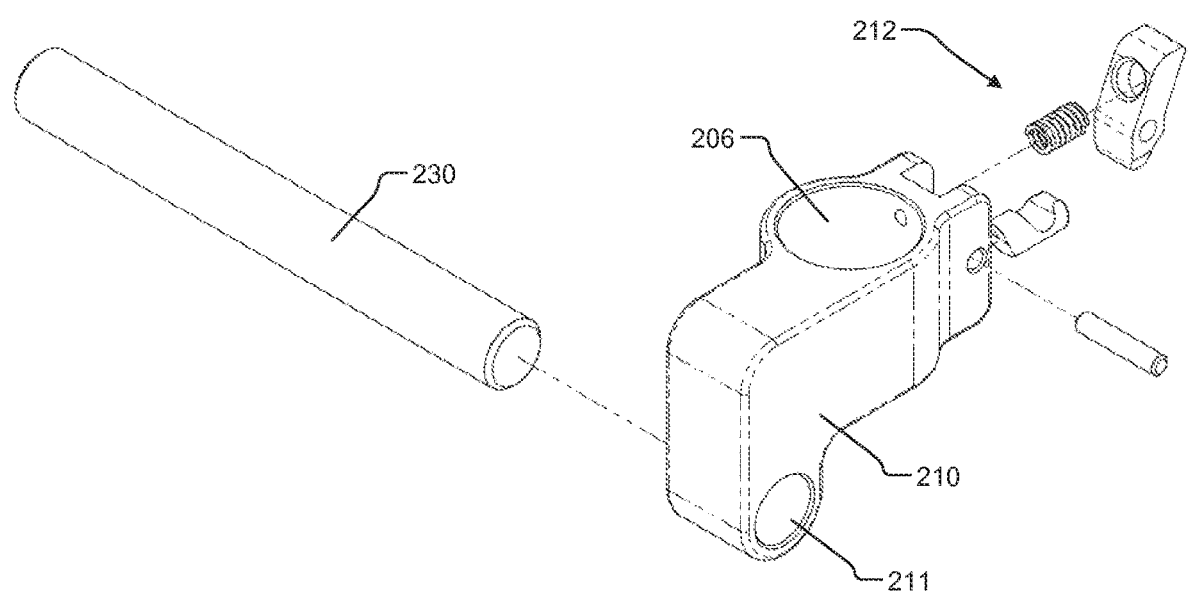
FIG. 28 is an exploded view of the first reduction assembly of FIG. 20.
Figure 29:
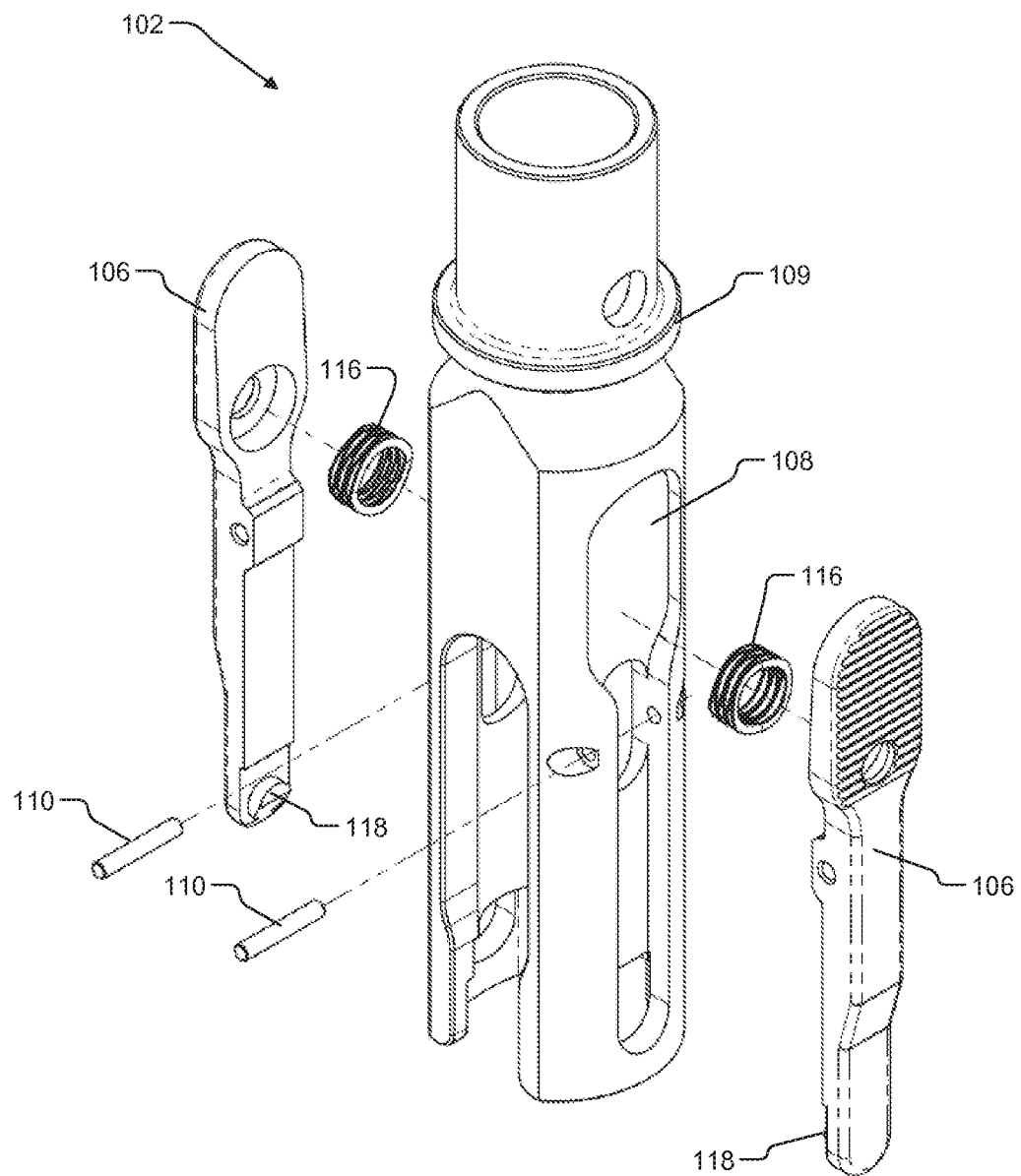
FIG. 29 is an exploded view of an exemplary reduction tower.
Figure 30:
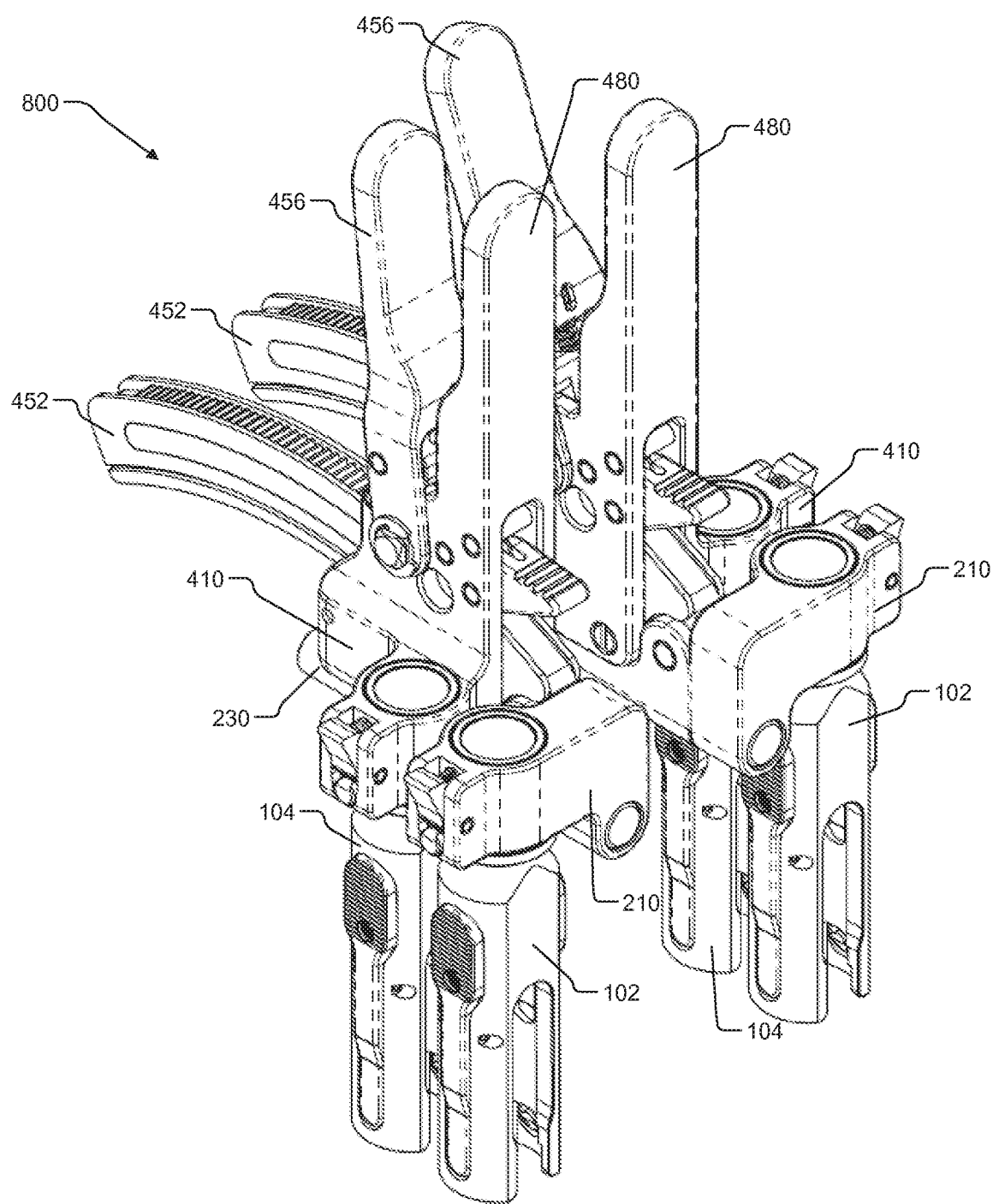
FIG. 30 is a perspective view of a pair of systems as shown in FIGS. 19A and 19B including right and left portions that are mirror images.

Referring now to FIG. 19A through FIG. 29, an assembly 800 for reduction of a spinal deformity includes similar features as the previously described embodiments. Like numerals are used for like features throughout. The exemplary assembly 800 depicted may be used alone or as a pair of assemblies including assembly 800 and a mirror image of assembly 800 as shown in FIG. 30. For ease of discussion, assembly 800 is described below with reference to attachment to the spine on a left side of the vertebrae. The assembly 800 includes features for attachment to tower assemblies 102 and 104 which may be referred to as a cephalad tower assembly 102 and a caudal tower assembly 104 described in greater detail with reference to FIG. 29.

Figure 22:
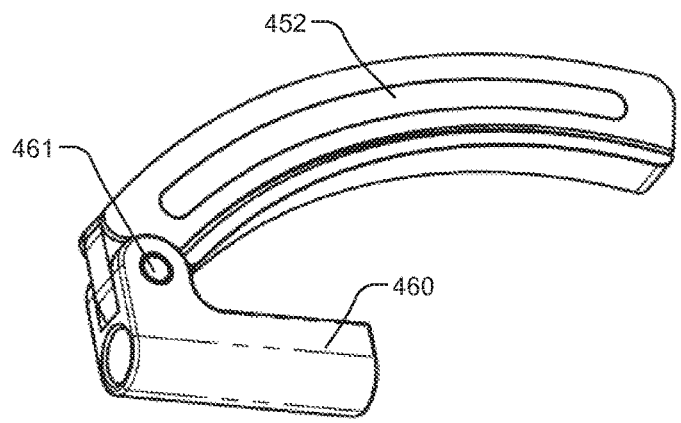
FIG. 22 is a perspective view of an arcuate rack gear with a pivotally coupled receiver.
Figure 23A:
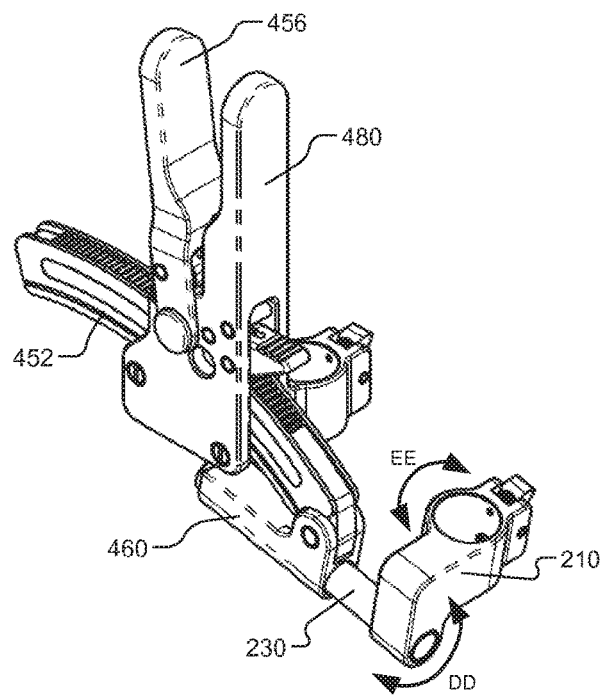
FIGS. 23A-23C, 24A-24C, and 25A-25C illustrate the reduction assembly of FIGS. 19A and 19B in various stages of reduction.
Figure 23B:
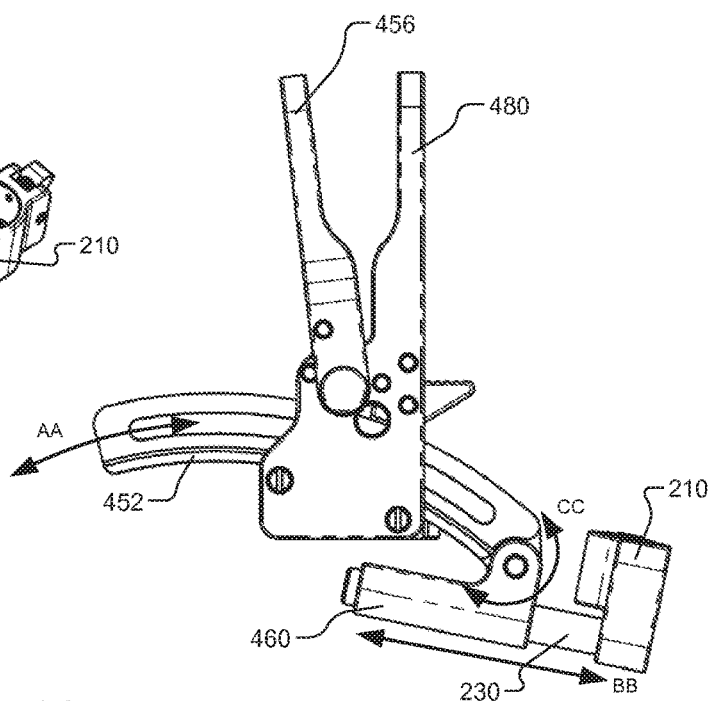
Figure 23C:
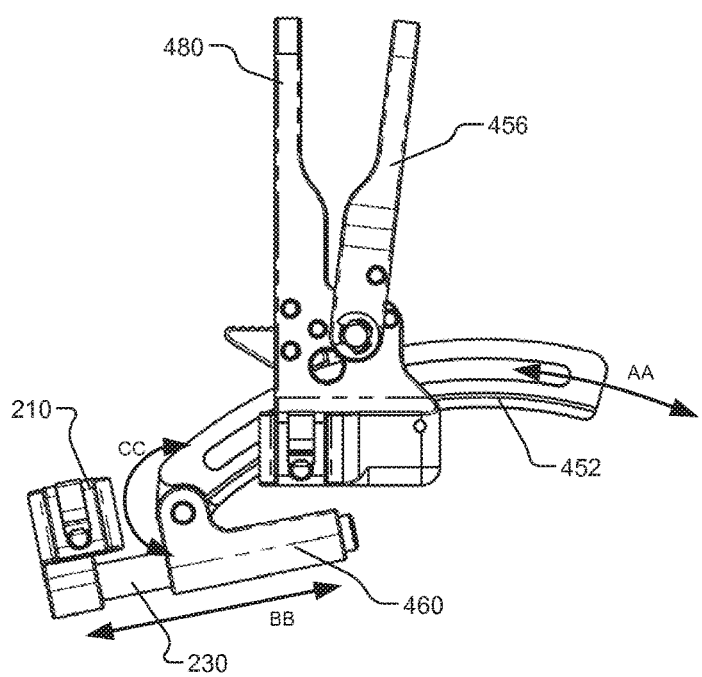
Figure 24A:
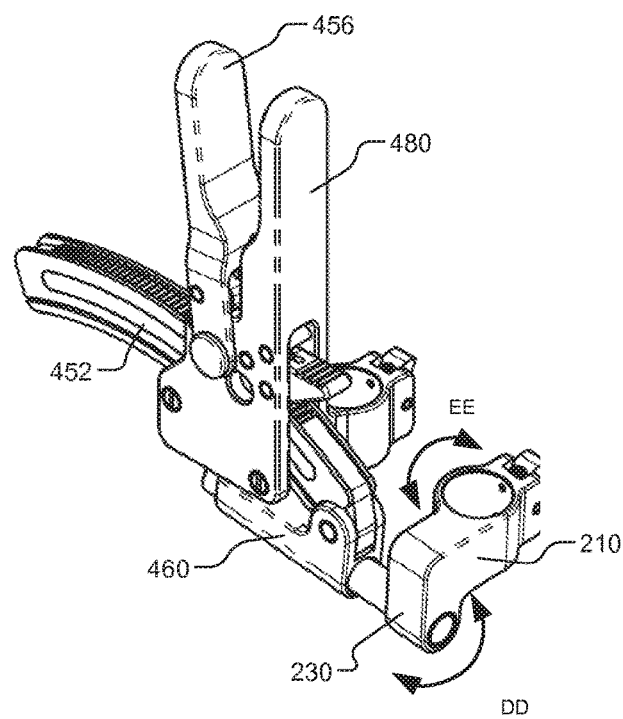
Figure 24B:
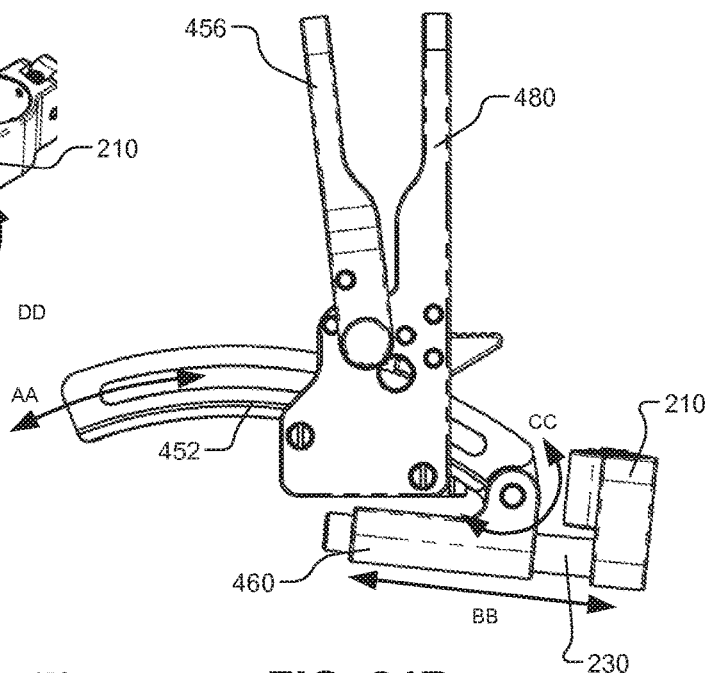
Figure 24C:
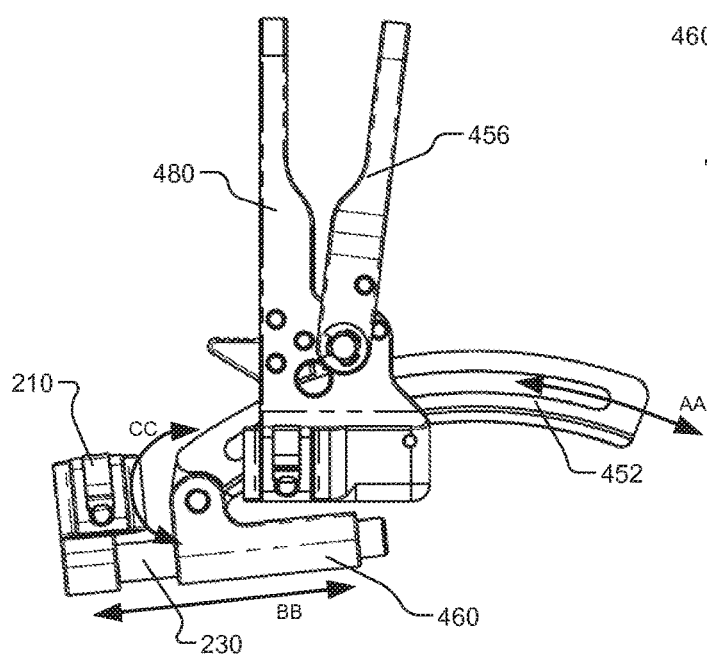
Figure 25A:
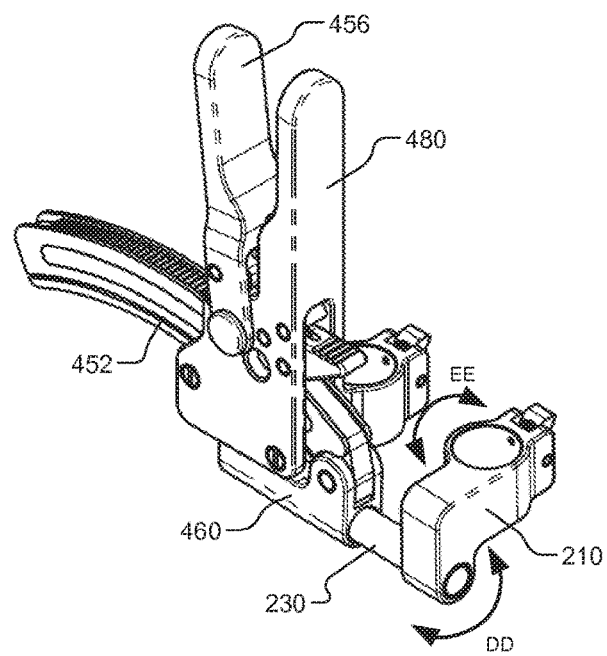
Figure 25B:
Figure 25C:
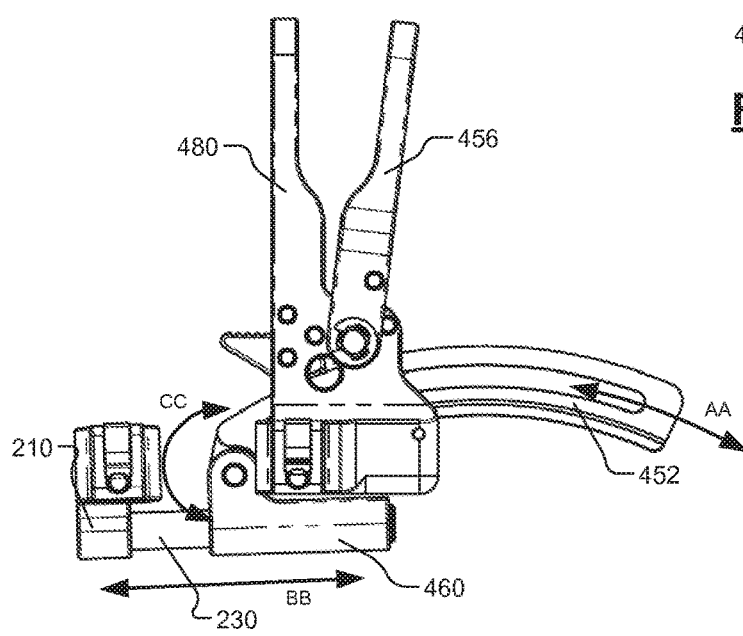

The assembly 800 includes first body member 210 and second body member 410 which may include the same or similar load transfer rings 206 and 406 respectively for attachment to the tower assemblies 102 and 104. The assembly includes the load transfer link 230 extending from the first body member 210 to the receiver 460 of the rack 452. The rack 452 may position the cephalad tower assembly 102 relative to the caudal tower assembly 104 simultaneously in multiple planes and directions. A drive system 850 similar to the drive system 450 described above may couple with the rack 452. The drive system 850 includes a similar drive mechanism for ratcheted engagement of the rack 452 via lever 456 which selectively engages and disengages the rack 452 to advance and lock the rack 452 in position. The reduction handle 480 may be used to apply a force to the lever 456 to advance the rack 452. The receiver 460 may be pivotally coupled to a distal end of the rack 452 to permit additional freedom of movement of the attached cephalad tower assembly 102. For example, as shown in FIG. 22, the rack 452 may be pivotally coupled with the receiver 460 by a pin 461.

Referring now to figure sets including FIGS. 23A-23C, 24A-24C, and 25A-25C, actuation of the assembly 800 demonstrates the multiple degrees or rotation and translation available for reducing a spinal deformity. The rack 452 may be advanced along an arcuate path AA in a first plane. The load transfer link 230 may slidably advance along a linear path BB within the receiver 460. The linear path BB may lie in the first plane or a parallel plane and along a common longitudinal axis shared by a bore in the receiver 460 and the load transfer link 230. The receiver 460 may rotate in a path CC about a distal end of the rack 452. The path CC may lie in the first plane or a parallel plane. The body member 210 may rotate in a circular path DD in a second plane normal to the longitudinal axis and substantially perpendicular to the first plane. For example, the body member 210 may be rotatable coupled to an end of the load transfer link 230. Alternately, the body member 210 may be fixed to the end of the load transfer link but may rotate freely within the receiver 460 for the same effect. Last, the cephalad tower assembly 102 (not shown) may rotate within the load transfer ring 206 in a circular path EE in a third plane that is substantially perpendicular to the second plane and the first plane.

Figure 26:
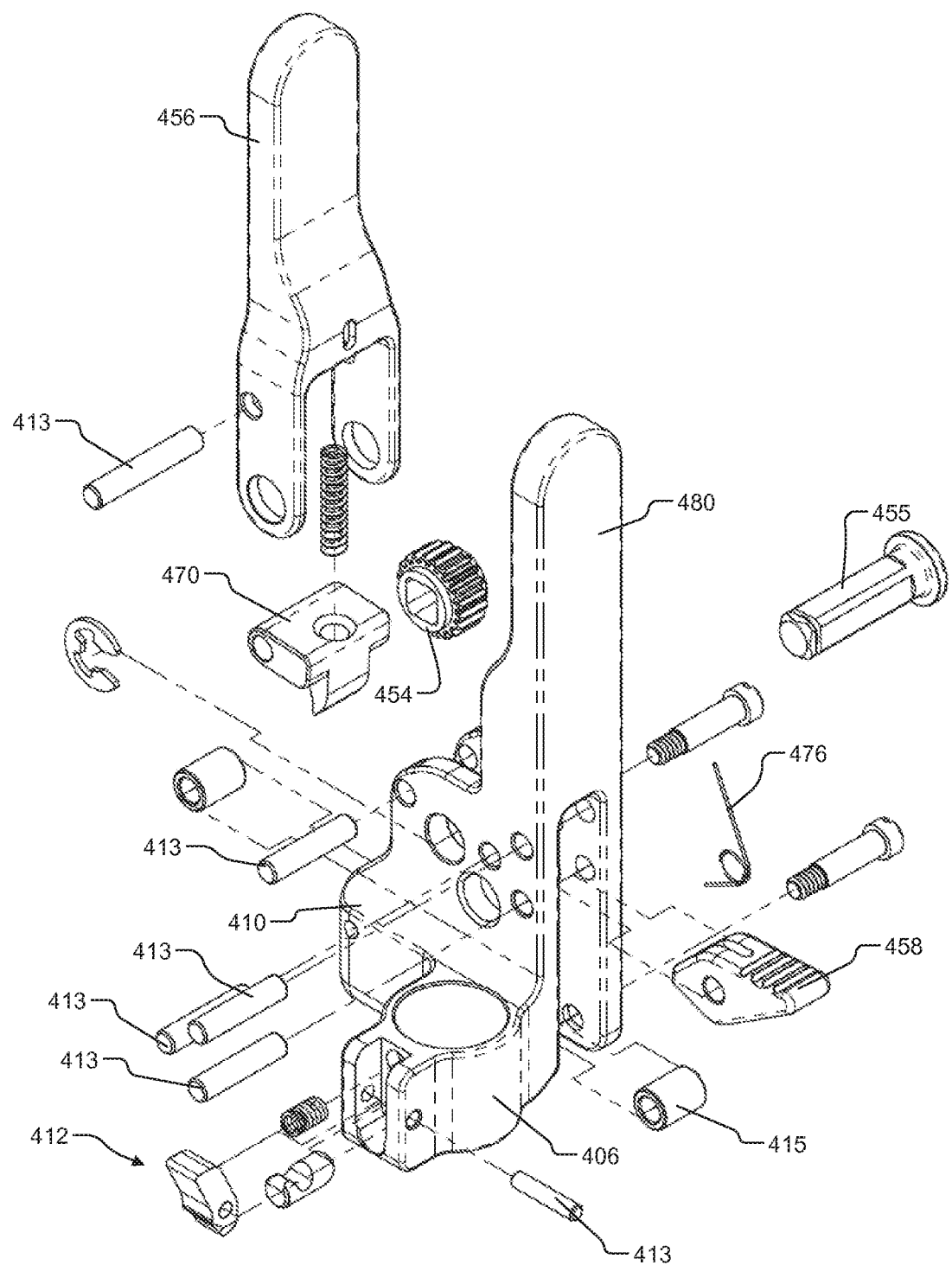
FIG. 26 is an exploded view of the second reduction assembly of FIG. 21.
Figure 27:
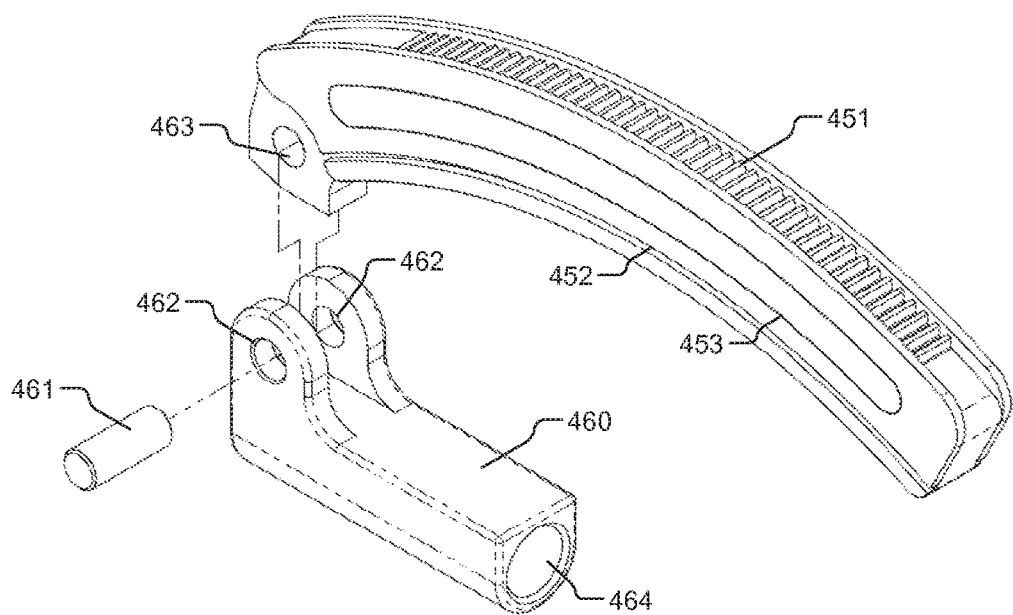
FIG. 27 is an exploded view of the arcuate rack gear and receiver of FIG. 22.

FIG. 26 illustrates an exploded view of the body member 410 and drive mechanism 450 of the assembly 800. FIG. 27 illustrates an exploded view of the rack 456 and receiver 460. FIG. 28 illustrates an exploded view of the body member 210 and load transfer link 230. FIG. 29 illustrates an exploded view of a tower assembly 102/104.

Referring now to FIG. 26, the reduction handle 480 may be offset from the load transfer ring 406 and extend parallel to a longitudinal axis of the load transfer ring 406. The reduction lever 456 may be pivotally coupled to the handle 480 by a pinion pin 455. The pinion pin may capture the pinion gear 454 within a portion of the reduction lever 456. Actuation of the reduction lever 456 thus turns the pinion gear 454 which in turn translates the rack 452. The locking pawl 458 may also be pivotally coupled to the reduction handle 480 by a guide pin 413. The locking pawl 458 may be biased into engagement with the rack 452 to lock the rack 452 in a predetermined position after advancement by the reduction lever 456. The reduction pawl 470 may be biased via spring 472 and allow movement of the rack 452 in a single direction as described above.

Referring now to FIG. 27, the rack 452 pivotally couples with the receiver 460 by engagement of a pivot pin 461 with bores 462 in an end of the receiver 460 and a bore 463 in an end of the rack 452. The rack 452 may further include a plurality of teeth 451 on a proximal surface for engagement with the pinion gear 454 and guide channels 453 on sides that engage portions of the body member 410 to guide the arcuate translation of the rack 452. In FIG. 28, the body member 210 may pivotally couple with the load transfer link 230 via a bore 211 in one end of the body member 210. The bore 211 may extend perpendicular to the load transfer ring 206.

FIG. 29 illustrates an exemplary tower such as the first or cephalad tower 102. The tower 102 may include all or some of the features as described above with reference to FIGS. 3A-3D. In other examples of the present invention, the towers may be of various shapes, sizes, lengths, etc. for various patient anatomies. The assembly 800 and any of the exemplary assemblies and instruments for spondylolisthesis reduction may be used with various styles of towers as the coupling features such as quick release mechanisms 212 and 412 may be modified for other styles of connections.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. A system for reducing deformities in a spine, comprising:
   a first tower assembly; a first reduction assembly, wherein the first reduction assembly is operably coupled to a proximal end of the first tower assembly;
   a second tower assembly positioned inferiorly relative to the first tower;
   a second reduction assembly, wherein the second reduction assembly is operably coupled to a proximal end of the second tower assembly, the second reduction assembly further comprising a reduction drive assembly, wherein the reduction drive assembly comprises a rack having an arcuate profile driven by a pinion gear, the rack having a center of rotation that is located posteriorly to the second tower;
   wherein the reduction drive assembly is operably coupled to the first reduction assembly via the reduction drive assembly, such that the reduction drive assembly transmits a leverage and causes relative movement of the first tower assembly from the second tower assembly from an unreduced state into a reduce state.

2. The system of claim 1, wherein the first reduction assembly further comprises a load transfer link receiver and the second reduction assembly further comprises a load transfer link member.

3. The system of claim 2, wherein the load transfer link member and the load transfer link receiver are operably engaged and freely translatable relative to one another.

4. The system of claim 2, wherein the load transfer link member is disposed at an end of the rack.

5. The system of claim 1, further comprising a locking lever operably coupled to the pinion gear.

6. The system of claim 1, wherein the first reduction assembly and the second reduction assembly are operably coupled by a load transfer link member, at least a portion of the member having stepped features to define a ratcheted portion, and a load transfer link receiver, at least a portion of the receiver being configured to engage the ratcheted portion of the member.

7. The system of claim 1, wherein the rack translates in a single plane relative to the second reduction assembly.

8. The system of claim 1, wherein the rack translates along a curved path having a center of rotation located at a position inferior to the second tower.

9. The system of claim 1, wherein the reduction drive assembly further comprises a reduction lever operably coupled to the pinion gear and the second reduction assembly further comprises a handle member.

10. The system of claim 9, wherein the reduction drive assembly further comprises a reduction pawl operably coupled to the reduction lever and the pinion gear and a locking pawl operably coupled to the rack.

11. A system for reducing deformities in a spine, comprising:
   a first tower assembly configured to attach to a first vertebra and extend in a posterior direction relative to the first vertebra;
   a first reduction assembly operably coupled to a proximal end of the first tower assembly;
   a second tower assembly configured to attach to a second vertebra and extend in a posterior direction relative to the second vertebra, the second vertebra being caudal to the first vertebra;
   a second reduction assembly operably coupled to a proximal end of the second tower assembly, the second reduction assembly further comprising a reduction drive assembly, wherein the reduction drive assembly comprises a rack having an arcuate profile driven by a pinion gear;
   wherein the reduction drive assembly is operably coupled to the first reduction assembly via the rack, such that the reduction drive assembly transmits a leverage and causes relative movement of the first vertebra from the second vertebra from an unreduced state into a reduce state.

12. The system of claim 11, wherein the first reduction assembly further comprises a load transfer link receiver and the second reduction assembly further comprises a load transfer link member.

13. The system of claim 12, wherein the load transfer link member and the load transfer link receiver are operably engaged and freely translatable relative to one another.

14. The system of claim 12, wherein the load transfer link member is disposed at an end of the rack.

15. The system of claim 11, further comprising a locking lever operably coupled to the pinion gear.

16. The system of claim 11, wherein the first reduction assembly and the second reduction assembly are operably coupled by a load transfer link member, at least a portion of the member having stepped features to define a ratcheted portion, and a load transfer link receiver, at least a portion of the receiver being configured to engage the ratcheted portion of the member.

17. The system of claim 11, wherein the rack translates in a single plane relative to the second reduction assembly.

18. The system of claim 11, wherein the rack translates along a curved path having a center of rotation located at a position caudal to the second vertebra.

19. The system of claim 11, wherein the reduction drive assembly further comprises a reduction lever operably coupled to the pinion gear and the second reduction assembly further comprises a handle member.

20. The system of claim 19, wherein the reduction drive assembly further comprises a reduction pawl operably coupled to the reduction lever and the pinion gear and a locking pawl operably coupled to the rack.

* * * * *